United States Patent
Zhao et al.

(10) Patent No.: US 6,653,331 B2
(45) Date of Patent: *Nov. 25, 2003

(54) TARGETED DRUG DELIVERY USING SULFONAMIDE DERIVATIVES

(75) Inventors: Zhiyang Zhao, Westerly, RI (US); Alfredo G. Tomasselli, Kalamazoo, MI (US); Kenneth A. Koeplinger, Portage, MI (US); Tillie Peterson, Portage, MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,469

(22) PCT Filed: Jul. 1, 1997

(86) PCT No.: PCT/US97/10817

§ 371 (c)(1), (2), (4) Date: Mar. 17, 1999

(87) PCT Pub. No.: WO98/00173

PCT Pub. Date: Jan. 8, 1998

(65) Prior Publication Data

US 2003/0109555 A1 Jun. 12, 2003

Related U.S. Application Data

(60) Provisional application No. 60/022,489, filed on Jul. 3, 1996.

(51) Int. Cl.[7] .................. A61K 31/18; A61K 31/44; A61K 38/19; C07D 277/62
(52) U.S. Cl. .................. 514/344; 514/347; 514/367; 514/603; 514/604; 546/288; 546/293; 548/166; 564/87; 564/92
(58) Field of Search .................. 546/288, 293; 548/166; 564/87, 92; 514/344, 347, 367, 603, 604

(56) References Cited

U.S. PATENT DOCUMENTS

| | | | | |
|---|---|---|---|---|
| 3,674,843 A | * | 7/1972 | Shen et al. .................. | 260/519 |
| 4,665,227 A | * | 5/1987 | Colatsky et al. .................. | 564/87 |
| 4,902,698 A | * | 2/1990 | Cooper et al. .................. | 514/351 |
| 4,948,809 A | * | 8/1990 | Witte et al. .................. | 514/538 |
| 5,025,025 A | * | 6/1991 | Bhagwat et al. .................. | 514/340 |
| 5,143,937 A | * | 9/1992 | Lang et al. .................. | 514/603 |
| 5,206,428 A | * | 4/1993 | Nakai et al. .................. | 562/427 |
| 5,292,756 A | * | 3/1994 | Duggan et al. .................. | 514/331 |
| 5,506,243 A | * | 4/1996 | Ando et al. .................. | 514/345 |
| 5,576,440 A | * | 11/1996 | Kehne et al. .................. | 546/294 |
| 5,610,320 A | * | 3/1997 | Yoshino et al. .................. | 549/72 |
| 5,663,174 A | * | 9/1997 | Dumont .................. | 514/252 |
| 5,859,281 A | * | 1/1999 | Sharpless et al. .................. | 560/12 |
| 5,955,505 A | * | 9/1999 | Takeo et al. .................. | 514/604 |
| 5,965,588 A | * | 10/1999 | Vazquez et al. .................. | 514/357 |
| 5,985,900 A | * | 11/1999 | Bender et al. .................. | 514/336 |
| 6,057,452 A | * | 5/2000 | Wuts et al. .................. | 548/215 |

FOREIGN PATENT DOCUMENTS

| | | | |
|---|---|---|---|
| WO | WO 93/14069 | * | 7/1993 |
| WO | WO 96/19455 | * | 6/1996 |
| WO | WO 97/42167 | * | 11/1997 |

OTHER PUBLICATIONS

Vargas et al., Chem. Abstract 124:76150, 1995.*
Ziegler et al., Chem. Abstract 119:195472, 1993.*
Woolhouse et al., Chem. Abstract 96:173871, 1982.*
Vischer, Chem. Abstract 91:89341, 1979.*
Fukuto et al., N,O–Diacylated–N–hydroxyarylsulfonamides, Biochemical And Biophysical Research Communications, vol. 187, No. 3, pp. 1367–1373, 1992.*
Schultz et al., Advanced Drug Delivery Reviews 26, pp. 91–104, 1997.*
Lee et al., Prodrugs of Nitroxyl as inhibitors of Aldehyde Dehydrogenase, J. Med. Chem., vol. 35, No. 20, 3648–3652, 1992.*
Cribb et al., Reactions of the nitroso and hydroxylamine metabolites, Drug Metabolism and Disposition, vol. 19, No. 5, pp. 900–906, 1991.*
Yijima et al., Chem. Abstract 95:219866, 1981.*
"Mechanism, Structure–Activity Studies, and Potential Applications of Glutathione S–Transferase–Catalyzed Cleavage of Sulfonamides", written by Zhiyang Zhao, Kenneth A. Koeplinger, Tillie Peterson, Robert A. Conradi, Philip S. Burton, Antonino Suarato, Robert L. Heinrikson and Alfredo G. Tomasselli, The American Society for Pharmacology and Experimental Therapeutics, vol. 27, No. 9, (1999).

* cited by examiner

*Primary Examiner*—Deepak Rao
(74) *Attorney, Agent, or Firm*—Arent Fox Kintner Plotkin & Kahn, PLLC

(57) ABSTRACT

The present invention relates to Glutathione S-transferase (GST)/Reduced Glutathione (GSH) as a means for the in-vivo release of a drug that has been conjugated to specific electrophilic moieties via a sulfonamide bond. The drug may be an anticancer agent (or one with other therapeutic properties) carrying a free —NH— which has been derivatized by the attachment of an electrophile containing a moiety, such as p-CN— or p-$NO_2$-pyridinylsulfonyl groups, or p-$NO_2$- or 2,4 dinitrophenylsulfonyl groups, or suitable derivatives thereof, to make a prodrug. Optionally, the sulfonamide moiety may have attached to it a targeting molecule. The present invention also provides Glutathione S-transferase (GST)/Reduced Glutathione (GSH) as a means for the release of a protected amino derivative that has been conjugated to specific electrophilic moieties via a sulfonamide bond. The precursor is a synthetic intermediate carrying a free —NH— which has been derivatized by the attachment of an electrophile via a sulfonamide bond.

5 Claims, No Drawings

TARGETED DRUG DELIVERY USING SULFONAMIDE DERIVATIVES

This is a national stage application of International Application No. PCT/US97/10817, filed Jul. 1, 1997, which claims the benefit of U.S. Provisional Application 60/022,489, filed Jul. 3, 1996.

FIELD OF THE INVENTION

The present invention relates to Glutathione S-transferase (GST)/Reduced Glutathione (GSH) as a means for the in-vivo release of a drug that has been conjugated to specific electrophilic moieties via a sulfonamide bond. The drug may be an anticancer agent (or one with other therapeutic properties) carrying a free —NH— which has been derivatized by the attachment of an electrophile containing a moiety, such as p-CN— or p-$NO_2$-pyridinylsulfonyl groups, or p-$NO_2$- or 2,4 dinitrophenylsulfonyl groups, or suitable derivatives thereof, to make a prodrug. The purpose of such a modification is to protect the free amino group, or to increase the drug solubility or alter absorption or distribution, or to improve some other physical, chemical, and pharmacological properties. Inside cells the prodrug is recognized and bound by GST which catalyses sulfonamide cleavage to release the active drug. Optionally, the sulfonamide moiety may have a targeting molecule attached to it.

The present invention also provides novel sulfonamide derivatives as a generic method adapted for —NH— protective groups in organic synthesis. Moreover, the invention relates to Glutathione S-transferase (GST)/Reduced Glutathione (GSH) as a means for the release of a protected amino derivative that has been conjugated to specific electrophilic moieties via a sulfonamide bond. The precursor is a synthetic intermediate carrying a free —NH— which has been derivatized by the attachment of an electrophile via a sulfonamide bond. The purpose of such a modification is to protect the free amino group during the chemical synthesis. The protected intermediate is recognized and bound by GST which catalyses the nucleophilic attack of GSH to the electrophilic part of the protected intermediate in a process that releases the desired intermediate harboring the free amino group under mild experimental conditions.

BACKGROUND OF THE INVENTION

A recent review article by J. D. Hayes and D. J. Pulford, Crit. Rev. Biochem. Mol. Biol. (1995) 30(6): 445–600, provides an illuminating overview of the GST supergene family and a detailed account of the individual isozymes' roles in protection against toxic agents and oxidative stress; it also offers insights into the various isozymes' regulation in diseased tissues, especially in cancer, and into their mechanisms of catalysis.

GST are enzymes ubiquitously present in living organisms. In mammals, GST are a large family of isozymes which are important components of the armamentarium of defense mechanisms that the cells use as a protection against foreign toxic chemicals and products of the oxidative stress. A variety of GST isozymes has been purified and extensively studied from rat and human organs, the most widely studied species. On the basis of amino acid sequence, the GST isozymes have been classified in five separate classes: alpha (A), mu (M), pi (P), sigma (S), and theta (T), that are abbreviated here by the use of the single letters indicated in parenthesis; each letter is then coupled to a number, e.g., A1, A2, A3, etc. to indicate the various gene products of class alpha subunits. In general, GST isozymes that have more than 40% identity in their amino acid sequences are assigned to the same class. The cytosolic GST of all mammalian isozymes are homodimers or heterodimers composed of subunits of Mr~23,000–26,000 that are catalytically independent; here the homodimer between two A1 subunits is indicated by the abbreviation GSTA1-1, and the formation of an heterodimer between the subunits A1 and A2 is abbreviated by GSTA1-2. The GST isozymes are distributed in various tissues, though some classes, or specific components of a class, are absent in particular organs. Human liver, is an abundant source of GST class alpha isozymes, but does not express specific class mu enzymes that are present in muscle, testis, and brain. Moreover, the distribution of GST isozymes varies in certain populations, e.g., among the three alleles present in the locus for human GSTM1 (GSTM1*A, GSTM*B, and GSTM1*0), the frequency of GSTM1*0 homozygosity is 22% in Nigerians, much lower than the 58% observed in the Chinese, 52% in the English, 48% in the Japanese, and 43% in the French populations. Moreover, the level of specific isozymes varies in relation to the diseased state of the cell, e.g., GSTP1-1 is overexpressed in various human tumors, including carcinoma of the lung, ovary, pancreas, stomach, colon, kidney, and esophagus. In keeping with their roles as detoxifying agents, GST isozymes are induced by the cell in response to xenobiotics and products of the oxidative stress.

Reduced Glutathione (GSH), the tripeptide γ-Glu-Cys-Gly, widely used by mammalians to maintain their redox conditions, is the indispensable substrate that the GST family uses to catalyze a large number of reactions. The active site of cytosolic GST harbors a GSH specific binding site (the G-site), and a second site (the H-site) that accommodates a broad variety of hydrophobic substrates and endows this family of isozymes with the ability to exhibit various catalytic activities. The three-dimensional structure of the class alpha, mu, pi, sigma, and theta of GST revealed the presence of two domains in each subunit: the N-terminal domain, that in class alpha encompasses residues 1 to 78, contains most of the residues that form the G-site; while the C-terminal domain, that in class alpha comprises residues 86 to 222, houses most of the H-site. When the primary structures of the family members are compared, the H-site is much more variable than the G-site; this justifies the specificity of the G-site for GSH observed for all GST isozymes, and the differences observed between the family members for their H-site substrate specificity and inhibitor sensitivity. X-ray crystallography, and site-directed mutagenesis data have produced important information on GST mechanism of catalysis and on the residues that determine the catalytic specificity of the various isozymes for GSH, at the G-site, and for particular electrophiles, at the H-site. The key to GST catalytic mechanism is its ability to lower the $pK_a$ of the sulphydryl group of its bound substrate GSH from 9.0, in aqueous solutions, to about 6.5. This property favors the formation of the $GS^-$ anion which promotes, at physiological pH, nucleophilic attack to the electrophilic center of the compound bound to the H-site. The electrophilic center resides on a carbon, a nitrogen, or a sulfur atom to which $GS^-$ becomes conjugated during catalysis via a thioether bond. Conserved $Tyr_9$ (in class alpha) is the residue responsible for the abstraction of a proton from GSH leading to the formation of the $GS^-$ thiolate at the G-site. Moreover, the conserved $Asp_{101}$ (in class alpha), at the G-site, is also implicated in catalysis. The functions of various residues in specific subunits have been assigned; for example in the rat class alpha, subunit $A_5$, $Tyr_{108}$ and $Asp_{208}$ have been implicated in conferring to this subunit the high stereospecific activity for aflatoxin $B_1$ exo-8,9-epoxide. While in the class mu enzymes $V_9$ and $I_{111}$ are the residues involved in the stereoselectivity and $Tyr_{115}$ in the activity toward epoxides. The selectivity of specific GST isozymes for particular substrates, and the presence of so many isozymes make it possible for the cells to cope with a multitude of noxious chemicals. The majority of the GST substrates are xenobiotics or products of oxidative stress that, upon conjugation to $GS^-$, are less reactive than the parent compounds, therefore less toxic, and, because of their partnership with GSH are expelled from the cells by the action of the Glutathione S-conjugate pumps (detoxification). In addition to its ability to catalyze the formation of a thioether bond between $GS^-$ and various electrophiles, GST exhibits glutathione peroxidase activity (reduction of organic hydroperoxides to their corresponding alcohols), and isomerase activity (e.g. the cis-trans isomerization of maleylilacetone to fumarylacetone). Yet, GST possess also non-catalytic binding activities, i.e. the ability to associate with a vast number of ligands, both covalently and non-covalently. This includes the fact that a variety of GST isozymes bind certain glutathione S-conjugates with higher affinity than that of the parent compounds.

Hays and Pulford, vide supra, have put together exhaustive information concerning the activities associated with the detoxification and activation of xenobiotics by GST isozymes, and the induction of GST isozymes by xenobiotics, including a detailed account of GST overexpression in drug-resistant and drug-sensitive cell lines. This information may be summarized as follows: (1) a variety of xenobiotics are GST substrates; (2) increased expression of GST isozymes translates into increased tolerance of the cell to xenobiotics; (3) GST isozymes are overexpressed in certain tumors; (4) GST isozymes are overexpressed in cell lines that are selected in-vitro for resistance to several drugs, e.g., Adriamycin, BCNU, Chlorambucil, Cyclophosphamide, Etoposide (VP16), Melphalan, and Vincristine; and (5) studies on cell lines from various cancer types have shown a correlation between GST expression and the level of drug resistance.

International Publication Number WO 95/31468, published Nov. 23, 1995, and International Publication Number WO 94/26307, published Nov. 24, 1994, are related to macrophage inhibition factor (MIF) as a target for pharmacological therapies in the areas of cancer and inflammatory diseases.

INFORMATION DISCLOSURE

Formation of amines via metabolic N—S bond cleavage of sulfonamides is an unusual observation. P. A. Crooks, Sulphonamides. In: L. A. Damani, editor. Sulfur-Containing Drugs and Related Organic Compounds: Chemistry, Biochemistry, and Toxicology, Vol. 1, Part B. Metabolism of Sulphur-Functional Groups. Chichester, West Sussex, England: Ellis Horwood Limited. 1989: 181–194.

In contrast to amides, sulfonamides are normally very resistant to either chemical or enzymatic hydrolysis and/or oxidative cleavage. Chemically, harsh conditions (eg: strong mineral acids, dissolving metal reductions) are usually required to cleave sulfonamides to liberate the corresponding amines. T. W. Greene, P. G. M. Wuts, Protective Groups in Organic Synthesis, 2nd ed. New York: John Wiley, 1991, 379–385.

The unusual in vivo biotransformation of the activated benzothiazole-2-sulphonamide to give the corresponding glutathione conjugate, mercapturic acid, mercaptan, and S-glucuronide as metabolites are disclosed in the following references: P. A. Crooks, Sulphonamides. In: L. A. Damani, editor. Sulfur-Containing Drugs and Related Organic Compounds: Chemistry, Biochemistry, and Toxicology, Vol. 1, Part B. Metabolism of Sulphur-Functional Groups. Chichester, West Sussex, England: Ellis Horwood Limited. 1989: 181–194 (also cited above); J. W. Clapp, A New Metabolic Pathway for a Sulphonamide Group, J Biol Chem 233: 207–214 (1956); and D. F. Colucci, D. A. Buyske, The Biotransformation of a Sulphonamide to a Mercaptan and to a Mercapturic Acid and Glucuronide Conjugate, Biochem Pharmacol 14: 457–466 (1965).

More recently the chemical reaction of GSH with similar benzothiazole or imidazole 2-sulfonamides to give the glutathione adduct, sulfur dioxide, and ammonia was reported in C. W. Conroy, H. Schwann, T. H. Maren, The Nonenzymic Displacement of the Sulfamoyl Group from different classes of aromatic compounds by Glutathione and Cysteine, Drug Metab Dispos 12: 614–618 (1984).

Suprisingly, these references did not indicate enzymatic catalysis of the observed cleavage reactions. This last reference suggested a basic GSH chemical reaction mechanism. However, the enzymatic catalysis according to the present invention is important since the reaction is catalyzed by at least an order of magnitude in the presence of GST over the processes disclosed in these references. At intracellular pH and GSH concentration, the enzymatic reaction of the present invention is likely to be dominant in comparison to direct chemical reaction with GSH as was done in the prior art references above.

In the prior art, the sulfonamide is known as one of the most stable nitrogen protective groups. Alkylsulfonamides are too stable to be used as protective groups. Arylsulfonamides are stable to alkaline hydrolysis and to catalytic reduction; they are cleaved by $Na/NH_3$, $Na/C_4H_9OH$, and by refluxing in acid (T. W. Green, and P. G. M. Wuts, Eds. Protective Groups in Organic Synthesis. John Wiley & Sonss, Inc. p 379 (1991). Due to the harsh deprotection conditions required, the utility of sulfonamides as protective groups for amines is very limited.

A recent report by Fukuyama suggests synthetic utility in the protection of secondary amines as 2- and 4-nitrobenzene sulfonamides. T. Fukuyama, C-K Jow, M. Cheung, 2- and 4-Nitrobenzenesulfonamides: Exceptionally Versatile Means for Preparation of Secondary Amines and Protection of Amines, Tetrahedron Letters 36(36): 6373–6374 (1995). The latter sulfonamides were found to be sufficiently activated as to be cleaved chemically by thiols (eg, propane thiol) in the presence of base. This results in the deprotection to re-release the secondary amine under relatively mild conditions (as compared to that normally required to cleave a sulfonamide bond). In editorial comments, Sharpless has suggested that Fukuyama's sulphonamide protection/deprotection scheme has enormous potential in synthetic chemistry. G. Li, H-T Chang, K. B. Sharpless, Catalytic Asymmetric Aminohydroxylation (AA) of Olefins. Angew Chem Int Ed Engl 35(4): 451–456 (1996); and Aminohydroxylation: Catalytic Asymmetric Reaction Achieved. Chemical and Engineering News 6–7 (Feb. 19, 1996). However, because of the similar pKa of the thiol S—H group and the sulfonamide N—H, the chemical deprotection step disclosed in this reference apparently is useful only for secondary amines which do not have an acidic N—H hydrogen in the protected sulfonamide product. This method is not suitable for primary amines because the required base used to generate thiolates from the corresponding thiols will also deprotonate the —NH— of sulfonamide bonds from primary amines. Thus, the sulfonamide protective group for primary amines cannot be deprotected by this procedure.

The GST/GSH catalysis of the present invention results in the desired deprotection for either primary or secondary amines by selectively lowering the pKa of GSH at neutral pH under which conditions the sulfonamide N—H (derived from primary amines) remains protonated and thus cleavable.

The chemical reaction of reduced glutathione (GSH) with an activated aromatic sulfone has also been reported in N. D. Heindel, R. A. Egolf, J. S. Stefely, Effect of Liposome and Cyclodextrin Entrapment on Retardation of Glutathione Decomposition of Nitroimidazoyl Sulfones. Journal of Pharmaceutical Sciences, 79(10): 862–865 (1990). According to the process of the present invention, similarly activated sulfones are cleaved by GST/GSH, thus demonstrating the generality of the reaction of the present invention for activated aromatic sulfones as well as sulfonamides.

International Publication WO 9508563 (Terrapin Technologies, Inc. USA), "Preparation of Glutathione Analogs Useful for Characterizing and Inhibiting Glutathione Transferases," discloses the use of GSH derivatives (e.g., alkyl-, alkenyl-, aralkyl-type esters, amides and mixed ester-amides) as GST inhibitors to potentiate chemotherapeutic agents in tumor cells.

International Publication WO 9509866 (Terrapin Technologies, Inc. USA), "Preparation of Glutathione S-Transferase-Activated Compounds as Drugs," discloses GST activation of prodrugs which were linked with GSH derivatives by amides, esters, and mixed amide/esters. No sulfonamide linkage is disclosed therein.

Ethacrynic Acid, an approved Merck & Co. diuretic drug, has been shown to deplete intracellular GSH and inhibit GST activity. Published results of Phase II clinical trials with ethacrynic acid in cancer patients suggest that the drug may be of utility in reversing the resistance of tumors to cytotoxic chemotherapy. Ethacrynic acid is structurally unrelated to the sulfonamides of the present invention.

In Acta. Pharm. Nordica 1(1) 1989, two N-sulfonyl pseudourea derivatives, ethyl N-(p-tolylsulfonyl)-1-pyrrolidinecarboximidate and 3-butyl-2-ethyl-1-p-tolylsulfonylpseudourea, were prepared and evaluated as potential prodrug forms for the primary sulfonamide group in the model p-toluenesulfonamide. It was concluded that N-sulfonyl pseudoureas, which are structurally different from the compounds of the present invention, are too stable to be considered as a potentially useful prodrug form for the primary sulfonamide group.

U.S. Pat. No. 5,037,883 discloses a polymeric drug comprising an inert synthetic polymeric carrier combined through aminoacid or peptide spacers with a bioactive molecule, a targeting moiety, and an optional cross-linkage. Derwent Abstract Accession Number 96-151152/15 discloses new prodrugs for the delivery of antitumor and antiinflammatory agents which cannot enter cells until cleaved by extracellular target cell enzyme. Derwent Abstract Accession Number 91-252432/34 discloses conjugates for treating tumors, for example, carcinoma, which comprises target cell specific- and enzymatically active-portion generating cyanide from a cyanogenic prodrug. Derwent Abstract Accession Number 90-253853/33 discloses activating a prodrug at a target tissue site by administering a conjugate comprising an activator linked to a targeting molecule, and administering a prodrug that is converted to an active drug by the activator.

Derwent Abstract Accession Number 97-020794/02 discloses the in vivo detection of tumors with imaging agent coupled to folate or its receptor binding analogue; new complexes for the process are also disclosed. U.S. Pat. Nos. 5,108,921 and 5,416,016 discloses a method for enhancing transport of an exogenous molecule across a membrane of a living cell by contacting the membrane with the exogenous molecule completed with a ligand selected from, for example, biotin or analogues, biotin-receptor-binding ligand, folate or analogues, folate receptor-binding ligand, niacin or analogues, niacin receptor-binding ligand, pantothenic acid or analogues, and many others, from a time sufficient to permit transmembrane transport of the ligand complex. Derwent Abstract Accession Number 90-334845/44 discloses enhancing across membrane transport of exogenous molecules into plant cells by complexing with water soluble vitamin or vitamin receptor binding agent.

SUMMARY OF THE INVENTION

The present invention particularly provides:

A compound of the formula I $$D_1\text{-}A_1 \qquad\qquad I$$

wherein $D_1$ is a drug having a —NH— functional group;
wherein $A_1$ is a moiety having a sulfonyl group attached to an optionally substituted phenyl or optionally substituted 5- or 6-membered heterocyclic ring;
wherein the phenyl or heterocyclic ring has an electron-withdrawing group; and
wherein the nitrogen atom of $D_1$ is bonded to the sulfur atom of $A_1$.

A compound of the formula I $$D_1\text{-}A_1 \qquad\qquad I$$

wherein $D_1$ is a drug having a —NH— functional group, the nitrogen atom of the group being covalently bonded to the sulfur atom of an $A_1$ moiety;
wherein the $A_1$ moiety is:

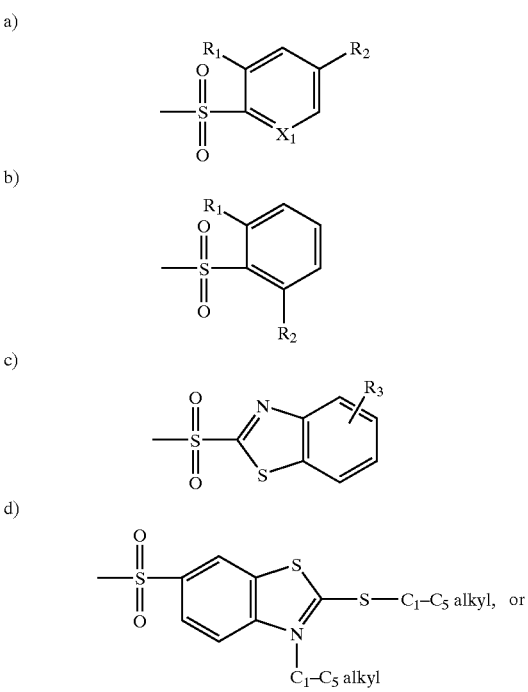

e)

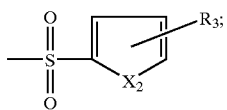

wherein $X_1$ is
  a) —C—, or
  b) —N—;
wherein $X_2$ is
  a) —N—, or
  b) —S—;
wherein $R_1$ is
  a) —H,
  b) —$NO_2$,
  c) —Cl,
  d) —$CF_3$, or
  e) —CN;
wherein $R_2$ is
  a) —H,
  b) —$NO_2$,
  c) —Cl,
  d) —$CF_3$, or
  e) —CN;
wherein $R_3$ is
  a) —H,
  b) —$C_1$-$C_5$ alkyl,
  c) —O—$C_1$-$C_5$ alkyl,
  d) —OH,
  e) —$NH_2$,
  f) —COOH, or
  g) —SH;
or a pharmaceutically acceptable salt thereof;
with the following proviso:
  1) $R_1$ and $R_2$ are not both —H.
The compound of formula I with the following additional provisos:
  2) $R_1$ and $R_2$ are not both —Cl;
  3) when one of $R_1$ or $R_2$ is —Cl, then the other is —$NO_2$ or —CN;
  4) when $R_2$ is —CN, and $R_1$ is —H, then $X_1$ is —N—;
  5) when $R_2$ is $CF_3$ and $R_1$ is —H, then $X_1$ is —N—.

The compound of formula I wherein the drug is an antineoplastic, antiviral, anticonvulsant, antidepressant, antibiotic, anesthetic, anti-inflammatory steroid, nonsteroidal anti-inflammatory agent, hypotensive, narcotic, anticholinergic, stimulant, sex hormone or prostaglandin.

The compound of formula I wherein the drug is selected from the compounds in Charts B, C or D.

The compound of formula I wherein $A_1$ is selected from the moieties in Chart A.

The compound of formula I wherein $A_1$ is the moiety a), $R_2$ is —CN, $R_1$ is —H, and $X_1$ is —N—.

The compound of formula I wherein $A_1$ is the moiety a), $R_2$ is —$NO_2$, $R_1$ is —H, and $X_1$ is —N—.

The compound of formula I where $A_1$ is the moiety a), $R_1$ and $R_2$ are both —$NO_2$, and $X_1$ is —C—.

The compound of formula I wherein $A_1$ is the moiety a), $R_2$ is —$NO_2$, $R_1$ is —H, and $X_1$ is —C—.

The compound of formula I selected from the compounds of Chart E.

Another aspect of the present invention is the following:
A process for deprotecting a compound of the formula II $$E_1\text{-}A_1 \quad\quad II$$

wherein $E_1$ is a compound having a —NH— functional group, the nitrogen atom of the group being bonded to the sulfur atom of an $A_1$ moiety;
wherein the $A_1$ moiety is:

a)

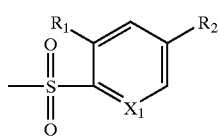

b)

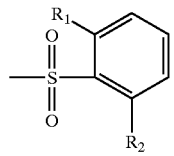

c)

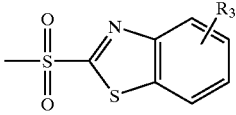

d)

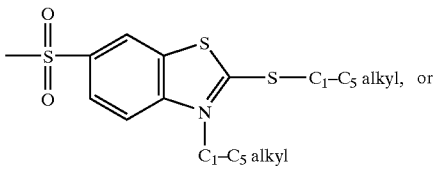

e)

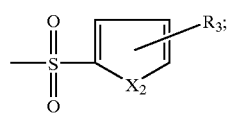

wherein $X_1$ is
  a) —C—, or
  b) —N—;
wherein $X_2$ is
  a) —N—, or
  b) —S—;
wherein $R_1$ is
  a) —H,
  b) —$NO_2$,
  c) —Cl,
  d) —$CF_3$, or
  e) —CN;
wherein $R_2$ is
  a) —H,
  b) —$NO_2$,
  c) —Cl,
  d) —$CF_3$, or
  e) —CN;
wherein $R_3$ is
  a) —H,
  b) —$C_1$-$C_5$ alkyl,
  c) —O—$C_1$-$C_5$ alkyl, d) —OH,
e) —NH$_2$,
f) —COOH, or
g) —SH;
or a pharmaceutically acceptable salt thereof,
with the following proviso:
1) R$_1$ and R$_2$ are not both —H; which comprises:
a) reacting the compound of formula II with 0.5 to 2.0 mg/ml of Glutathione S-transferase (GST) and 50–500 μM of Reduced Glutathione (GSH) in an aqueous solution.

The above process with the following additional proviso:
2) R$_1$ and R$_2$ are not both —Cl.

The above process wherein the reaction is carried out in an aqueous solution with a water miscible organic solvent.

The above process which further comprises:
b) isolating the deprotected compound of formula III

E$_1$-H    III by extraction with organic solvents.

The above process having a concentration of acetonitrile up to 30%.

The above process wherein the reaction is carried out using 500 μM GSH with GST (0.5 mg protein/ml).

The above process wherein the reaction is carried out in a phosphate buffer.

The above process wherein the reaction is carried out at a pH of 5 to 8 and at a temperature of 20° to 50° C.

The above process wherein the pH is about 7.4 and the temperature is about 37° C.

The present invention also provides:
A compound of the formula

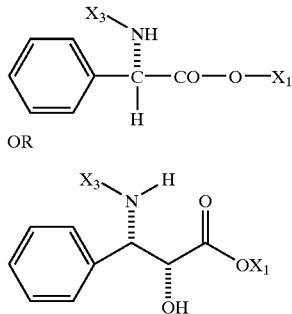

wherein X$_1$ is
1) —C$_1$-C$_8$ alkyl
2) —C$_5$-C$_7$ cycloalkyl, or
3) —CH$_2$-phenyl wherein the phenyl is optionally substituted with 1 or 2
    a) —O—X$_{1-1}$ wherein X$_{1-1}$ is C$_1$-C$_3$ alkyl
    b) —F, —Cl, —Br, —I.
wherein X$_3$ is
1) 2-chloro-4-nitrophenylsulfonyl,
2) 4-nitro-pyridinylsulfonyl,
3) 4-CN-pyridinylsulfonyl,
4) 2-CF$_3$-4-nitrophenylsulfonyl,
5) 4-CF$_3$-pyridinylsulfonyl, or
6) 2-benzothiazolsulfonyl.

The present invention also provides:
A method of using the compounds of formula I to deplete intracellular Reduced Glutathione (GSH) levels in vivo.

A method of using the compounds of Chart E to deplete intracellular Reduced Glutathione (GSH) levels in vivo.

The present invention also provides:
Use of a moiety having a sulfonyl group attached to an optionally substituted phenyl or optionally substituted 5- or 6-membered heterocyclic ring;
    wherein the phenyl or heterocyclic ring has an electron-withdrawing group;
    to prepare a prodrug of a drug having a —NH— functional group;
    wherein the nitrogen atom of the drug is covalently bonded to the sulfur atom of the moiety; and
    wherein the prodrug when administered to a mammal in need thereof will be directed toward a cell which is overexpressing GST.

The use wherein the moiety is:

a)
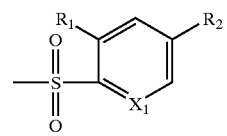

b)
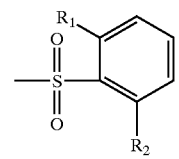

c)
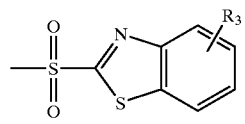

d)
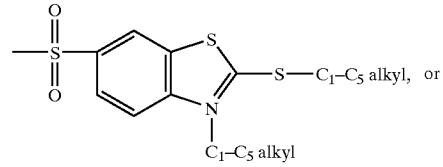

e)
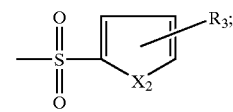

wherein X$_1$ is
    a) —C—, or
    b) —N—;
wherein X$_2$ is
    a) —N—, or
    b) —S—;
wherein R$_1$ is
    a) —H,
    b) —NO$_2$,
    c) —Cl,
    d) —CF$_3$, or
    e) —CN;
wherein R$_2$ is
    a) —H,
    b) —NO$_2$, c) —Cl,
d) —CF$_3$, or
e) —CN;
wherein R$_3$ is
a) —H,
b) —C$_1$–C$_5$ alkyl,
c) —O—C$_1$–C$_5$ alkyl,
d) —OH,
e) —NH$_2$,
f) —COOH, or
g) —SH;
or a pharmaceutically acceptable salt thereof;
with the following proviso:
1) R$_1$ and R$_2$ are not both —H.
The use with the additional provisos:
2) R$_1$ and R$_2$ are both —Cl;
3) when one of R$_1$ or R$_2$ is —Cl, then the other is —NO$_2$ or —CN;
4) when R$_2$ is —CN, and R$_1$ is —H, then X$_1$ is —N—;
5) when R$_2$ is CF$_3$ and R$_1$ is —H, then X$_1$ is —N—.
The use wherein the moiety is selected from the moieties in Chart A.
The use wherein the moiety is selected from the group consisting of:

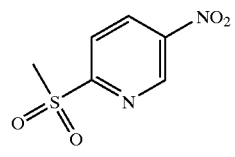

p-NO$_2$-pyridinylsulfonyl

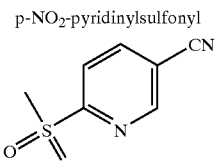

p-CN-pyridinylsulfonyl

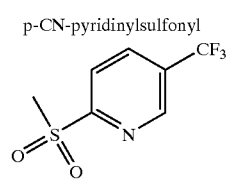

p-CF$_3$-pyridinylsulfonyl

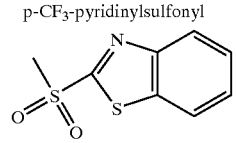

2-benzothiazolsulfonyl

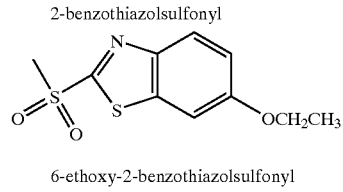

6-ethoxy-2-benzothiazolsulfonyl

The use wherein the drug is is an antineoplastic, antiviral, anticonvulsant, antidepressant, antibiotic, anesthetic, anti-inflammatory steroid, nonsteroidal anti-inflammatory agent, hypotensive, narcotic, anticholinergic, stimulant, sex hormone or prostaglandin.

The use wherein the drug is selected from the compounds in Charts B, C or D.

The use wherein the drug is doxorubicin or epirubicin.

The use wherein the prodrug is selected from the group of compounds in Chart E.

The use wherein the cell is a diseased cell.

The use wherein the diseased cell is a cancer cell.

The use which further comprises the moiety attached to a targeting molecule selected from the group consisting of: peptides, carbohydrates, glycosylated peptides, vitamins and hormones; through an ester, ether, amide, carbonate, carbamate or thiocarbonate linkage.

The use wherein the targeting molecule is selected from the group consisting of: cytokines, growth factors, insulin, monosaccharides, disaccharides, oligosaccharides, amino sugars, glucose, glucosamine, fucose, fucosamine, galactose, galactosamine, folic acid, vitamin B12, biotin, niacin, pantothentic, and steroid.

The use wherein the prodrug is selected from the group consisting of compounds in Chart K.

The present invention also provides:

A method of directing a drug having an —NH— functional group toward a cell overexpressing GST which comprises:

administering to a mammal in need thereof the drug attached to a moiety having a sulfonyl group attached to an optionally substituted phenyl or optionally substituted 5- or 6-membered heterocyclic ring;

wherein the phenyl or heterocyclic ring has an electron-withdrawing group; and wherein the nitrogen atom of the drug is covalently bonded to the sulfur atom of the moiety.

The method wherein the moiety is:

a)

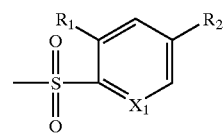

b)

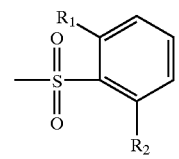

c)

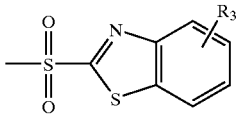

d)

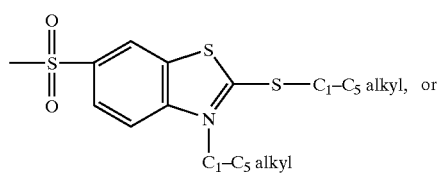

e)

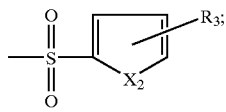

wherein $X_1$ is
  a) —C—, or
  b) —N—;
wherein $X_2$ is
  a) —N—, or
  b) —S—;
wherein $R_1$ is
  a) —H,
  b) —$NO_2$,
  c) —Cl,
  d) —$CF_3$, or
  e) —CN;
wherein $R_2$ is
  a) —H,
  b) —$NO_2$,
  c) —Cl,
  d) —$CF_3$, or
  e) —CN;
wherein $R_3$ is
  a) —H,
  b) —$C_1$–$C_5$ alkyl,
  c) —O—$C_1$–$C_5$ alkyl,
  d) —OH,
  e) —$NH_2$,
  f) —COOH, or
  g) —SH;
or a pharmaceutically acceptable salt thereof,
with the following proviso:
  1) $R_1$ and $R_2$ are not both —H.
The method with the additional provisos:
  2) $R_1$ and $R_2$ are both —Cl;
  3) when one of $R_1$ or $R_2$ is —Cl, then the other is —$NO_2$ or —CN;
  4) when $R_2$ is —CN, and $R_1$ is —H, then $X_1$ is —N—;
  5) when $R_2$ is $CF_3$ and $R_1$ is —H, then $X_1$ is —N—.
The method wherein the moiety is selected from the group moieties in Chart A.
The method wherein the moiety is selected from the group consisting of:

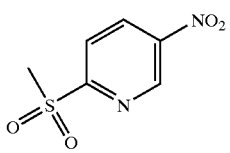

p-$NO_2$-pyridinylsulfonyl

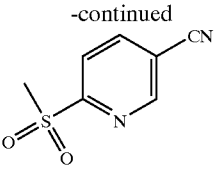

p-CN-pyridinylsulfonyl

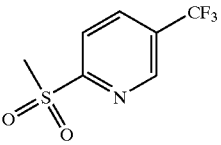

p-$CF_3$-pyridinylsulfonyl

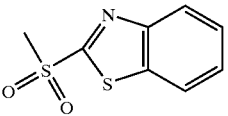

2-benzothiazolsulfonyl

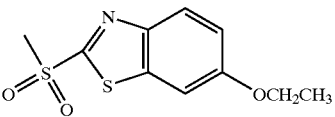

6-ethoxy-2-benzothiazolsulfonyl

The method wherein the drug is is an antineoplastic, antiviral, anti-convulsant, antidepressant, antibiotic, anesthetic, anti-inflammatory steroid, nonsteroidal anti-inflammatory agent, hypotensive, narcotic, anticholinergic, stimulant, sex hormone or prostaglandin.

The method wherein the drug is selected from the compounds in Charts B, C or D.

The method wherein the drug is doxorubicin or epirubicin.

The method wherein the resulting drug is selected from the group of compounds in Chart E.

The method wherein the cell is a diseased cell.

The method wherein the diseased cell is a cancer cell.

The method wherein the moiety is attached to a targeting molecule selected from the group consisting of: peptides, carbohydrates, glycosylated peptides, vitamins and hormones; through an ester, ether, amide, carbonate, carbamate or thiocarbonate linkage.

The method wherein the targeting molecule is selected from the group consisting of: cytokines, growth factors, insulin, monosaccharides, disaccharides, oligosaccharides, amino sugars, glucose, glucosamine, fucose, fucosamine, galactose, galactosamine, folic acid, vitamin B12, biotin, niacin, pantothentic, and steroid.

The method wherein the resulting drug is selected from the group of compounds in Chart K.

The present invention also provides:
A method of targeting a cell overexpressing GST, which comprises:
  administering to a mamal in need thereof a drug having an —NH— functional group attached to a moiety as described above. The method wherein the drug is as described above. The method wherein the resulting drug is as described in Chart E. The method wherein the cell is as described above. The method wherein the moiety is attached to a targeting molecule as described above. The method wherein the resulting drug with the targeting molecule is as described in Chart K.

The present invention also provides:
A compound selected from the group consisting of:

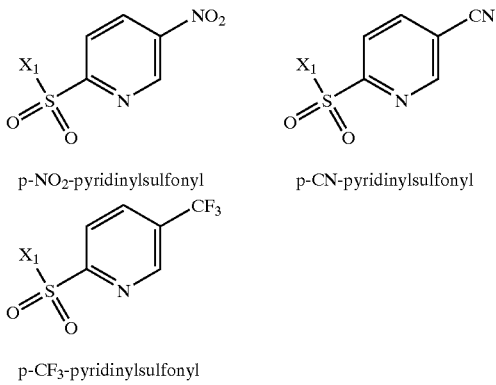

p-NO₂-pyridinylsulfonyl  p-CN-pyridinylsulfonyl p-CF₃-pyridinylsulfonyl wherein $X_1$ is F, Cl, Br or I.
Finally, the present invention provides:
The compound of formula IV $$D_1\text{-}A_1\text{-}T_1 \qquad \qquad IV$$

wherein $T_1$ is a targeting molecule selected from the group consisting of: peptides, carbohydrates, glycosylated peptides, vitamins and hormones; covalently bonded to the $A_1$ moiety through an ester, ether, amide, carbonate, carbamate or thiocarbonate linkage.

This compound wherein the targeting molecule is selected from the group consisting of: cytokines, growth factors, insulin, monosaccharides, disaccharides, oligosaccharides, amino sugars, glucose, glucosamine, fucose, fucosamine, galactose, galactosamine, folic acid, vitamin V12. biotin, niacin, pantothentic, and steroid. This compound wherein the resulting drug is selected from the group compounds in Chart K.

The present invention relates to attaching an electrophile containing a moiety, such as p-CN— or p-NO₂-pyridinylsulfonyl groups, or p-NO₂- or 2,4-dinitrophenylsulfonyl groups (or suitable derivatives thereof), listed in Chart A, to drugs carrying free amino groups, listed in Charts B–D, to make pro-drugs, examples of which are listed in Chart E, which are easily converted to the original drug inside a cell by the action of the ubiquitous GST via sulfonamide cleavage. An important application of the present invention is in cancer therapy where many anticancer agents containing free amino groups are used, and cancerous cells overexpress certain types of GST many-fold above the level expressed by normal cells. The overexpression of this enzyme is believed to be directly associated with the drug resistance of tumors. The application is even more valuable in those cases in which the continuous use of specific drugs, to treat certain forms of cancer, has generated cell resistance to those drugs and concomitant overexpression of particular GST isozymes.

The present invention also provides a procedure to release, under mild experimental conditions, the desired intermediate harboring the free amino group. In addition, the present invention provides a tool for stereoisomer isolation since the deprotection by GST/GSH is a stereoselective process. Protection of amino groups during the synthesis of many molecules, including a broad range of therapeutic agents, is of great importance in organic chemistry. However, deprotection disclosed in the prior art may create serious problems due to the brutality of the conditions necessary to bring the reaction to completion. The present invention provides a procedure for overcoming the disadvantages of the prior art processes.

The term "drug" as used herein means any substance intended for use in the diagnosis, cure, mitigation, treatment or prevention of disease or in the enhancement of desirable physical or mental development and conditions in man or animal.

The expression "drug having a —NH— functional group" as used herein means that the drug possesses at least one functional group which is capable of covalently bonding to the sulfur atom in the sulfonyl moiety in such a manner that a —NH— containing active drug species will ultimately be released at the desired site of action, e.g. the cancer cells. Such —NH— functional groups include amino, amide, azide, hydrazine, imide, urea, (carbamate) functions.

The expression "—NH—", as used herein, means that the compound or intermediate possesses at least one functional group which is capable of covalently bonding to the sulfur atom in the sulfonyl moiety in such a manner that a —NH— containing compound or intermediate will ultimately be recovered at the desired step of synthesis by GST/GSH catalyzed cleavage. Such reactive functional groups include amino, amide, azide, hydrazine, imide, urea, (carbamate) functions.

The word "amino" means a primary or second amino function, i.e. —NH₂ or —NHR. The secondary amino function is also represented herein as —NH—, particularly, since the exact identity of the R portion of —NHR is immaterial, R being a part of the drug residue itself which is left unchanged by conversion of the drug to the sulfonamide derivatives.

The word "amide" means, for example, a carbamoyl (—CONH₂) or substituted carbamoyl (—CONHR) or a sulfamoyl (SO₂NH₂) or substituted sulfamoyl (—SO₂NHR).

The word "targeting" means directing or guiding toward.

It will be apparent to one of ordinary skill in the art, from the known structures of the many drug species exemplified hereinbelow, that in many cases the selected drug possesses more than one reactive functional group, and, in particular, that the drug may contain amino or amide or other functional groups in addition to the groups to which the sulfonyl moiety will be linked, and that these additional groups will at times benefit from being protected during synthesis of linking to the sulfonyl moiety and/or administration. The protection may be or may be not deprotected after sulfonamide bond is established. Obviously, such protected drug species are encompassed by the definition of "drug" set forth hereinabove.

From the foregoing, it will also be apparent to one of ordinary skill in the art that many different drugs may be derivatized in accordance with the present invention. Numerous such drugs are specifically mentioned hereinbelow. However, it should be understood that the following discussion of drug families and their specific members for derivatization according to this invention is not intended to be exhaustive or to limit the present invention, but is merely illustrative:

Drugs having a —NH— functional group for use herein include, but are not limited to, antineoplastics (anticancer/antitumor agents), antivirals, anticonvulsants, antidepressants, antibiotics, anesthetics, antiinflammatory steroids, nonsteroidal antiinflammatory agents/analgesics, hypotensives, narcotic analgesics, narcotic antagonists and agonist/antagonists, CNS anticholinergics, neuroprotectant agents, stimulants, sex hormones, and CNS prostaglandins. Preferred drugs of this type are antineoplastics and neuroprotectant agents.

Among the antineoplastics, there are included, for example, those of the antifolates, 5-fluoropyrimidines, cytidine analogs, purine antimetabolites, hydroxyurea, antimicrotubule agents, alkylating agents, nonclassic alkylating agents, platinum analogs, bleomycin, antitumor antibiotics, anthracyclines, topoisomerase II inhibitors, and camptothecins.

Exemplary antifolates include methotrexate, tetrahydrofolate, aminopterin, trimethoprim, trimetrexate, pyrimethamine, 10-ethyl-10-deaza aminopterin, 5,10-dideazatetrahydrofolate, CB 3717, ZD 1694, and 1843U89.

Illustrative 5-fluoropyrimidine drugs include fluorouracil, ftorafur, fluorodeoxyuridine, and 5'-deoxyfluorouridine.

Illustrative csytidine analogs include cytidine, deoxycytidine, cytosine arabinoside, 5-azacytosine, 2',2'-difluorodeoxycytidine, and 5-azacytosine arabinoside.

Purine Antimetabolites include, for example, azathioprine, 6-mercaptopurine, 6-thioguanine, pentosatin, adenosine, cladribine, and fludarabine phosphate.

Antimicrotubule agents include, for example, vindesine, vincristine, vinblastine, taxol, and docetaxel.

Alkylating agents include, for example, melphalan, cyclophosphamide, ifosfamide, chloroethylnitrosourea, bis-chloroethylnitrosourea (BCNU), cyclohexylchloroethylnitrosourea (CCNU), and methylcyclohexylchloroethylnitrosourea (methyl-CCNU).

Nonclassic alkylating agents include, for example, procarbazine, dacarbazine, and temozolomide.

Platinum analogs include, for example, cisplatin, tetraplatin, carboplatin, platinum-dach, ormaplatin, oxaliplatin, and CI-973.

Bleomycin analogs include, for example bleomycin $A_2$, bleomycin $B_2$, and liblomycin.

Antitumor antibiotics include, for example, dactinomycin, and mitomycin C.

Illustrative anthracyclines and anthracendiones include doxorobicin, daunorubicin, epirubicin, idarubicin, and mitoxantrone.

Topoisomerase II inhibitors include, for example, m-AMSA (amsacrine), CI-921, Elliptinium.

Camptothecins include, for example, 9-aminocamptothecin.

Investigational anticancer agents include, for example, pyrazoloacridine, bizelesin, edatrexate, leucovorin, gemcitabine, cytarabine, CI-980, fenretinide, and TNP-470.

Examples of the above parent drug compounds are included in Charts B-D below by structure and name. All of these compounds are described in the reference: "Cancer Chemotherapy and Biotherapy: Principles and Practice," 2nd Ed., Bruce A. Chabner, M. D. and Dan L. Longo, M. D., Editors, Lippincott-Raven Publishers, Philadelphia—New York (1996), which is hereby incorporated by reference herein. These compounds are known in the art and their method of preparation would be readily available to one of ordinary skill in the art.

The prodrug sulfonamide derivatives of the present invention are prepared by a variety of synthetic procedures tailored to the structure of the particular drug to be derivatized, particularly to the nature of the reactive functional group to be linked to the sulfonyl moiety, and the presence of other functional groups which may benefit from protection.

In preferred embodiments of the present invention, the drug contains a —NH— group susceptible to direct bonding to the sulfur atom in the sulfonyl moiety. It is also preferred, for simplicity's sake, that the selected drug not require protection of other functional groups, although such groups may be protected when necessary.

The prodrug sulfonamide derivatives of the present invention are synthesized by reacting the drug with the appropriate sulfonyl chloride in the presence of an appropriate base in a nonalcoholic organic solvent, such as acetone, acetonitrile methylene chloride, or ethyl ether. The base may be an organic amine, such as aniline, triethylamine or pyridine or sodium carbonate or potassium carbonate. This synthetic procedure and many examples thereof are disclosed in International Publications WO 94/11361, published May 26, 1994, WO 94/18188, published Aug. 18, 1994, and WO 95/30670, published Nov. 16, 1995, all of which are incorporated by reference herein. In the process described above, the prodrug sulfonamide derivatives (examples of which are shown in Chart E below) are not always the only products obtained in significant amounts; yet other products of sulfonamide derivatives may be obtained which are encompassed by the present invention. The preparation of a sulfonyl chloride is shown in Preparation 1 and Chart F below. Those sulfonyl chloride moieties in Chart A, which are not commercially available, such as the pyridinyl-containing sulfonyl chlorides, are prepared by analogous procedures. A sulfur-containing precursor may also be oxidized to a sulfonyl-containing moiety of the present invention.

The rate of release of a given drug from the corresponding prodrug of the present invention by GST-catalyzed cleavage of the sulfonamide bond depends upon the sulfonamide moiety attached to the parent drug. A given prodrug containing a moiety with multiple electron withdrawing groups, e.g., 4-cyanopyridinylsulfonamide will be cleaved by GST to the parent drug faster than the corresponding prodrug bearing a modification with only one electron withdrawing group, e.g., 2, or 4-nitrophenylsulfonamide. The optimal rate of release of the parent drug may be achieved by choosing an appropriate modification in the prodrug. In certain circumstances, the sulfonamide moiety may temporarily mask the adverse effects of the drug.

Besides providing a biodegradable linkage, the sulfonamide moiety may confer improved solubility, bioavailability, cell penetration, or other therapeutic benefits. In certain circumstances, the sulfonamide moiety may temporarily mask the adverse effects of the drug. For example, the coupling of the sulfonamide moiety to an inherently cytotoxic agent may alter or reduce the agent's cytotoxicity until it is released within the target cell.

As noted above, various diseased cells, particularly certain cancer cells, overexpress GST. In addition, various diseased cells overexpress certain receptors (for example, cancer cells overexpress the folic acid, growth factor, and insulin-like receptors), and/or have the property of enhanced active uptake mechanisms for certain nutrients, such as sugars (for example, glucose, galactose and fucose) as compared to normal cells.

Optionally, according to the present invention, the sulfonamide moiety may have attached to it a targeting molecule. This targeting molecule is a ligand, which, by virtue of overexpressed receptors or unusually high uptake by the diseased cell, will enhance the prodrug's ability to accumulate preferentially in the diseased cell. See, for example, U.S. Pat. Nos. 5,108,921 and 5,416,016 which disclose the use of folic acid and biotin as targeting molecules.

Examples of such targeting molecules include the following: peptides, such as cytokines, growth factors and insulin; carbohydrates (monosaccharides, disaccharides, oligosaccharides, or amino sugars) and/or glycosylated peptides, such as glucose, glucosamine, fucose, fucosamine, galactose and galactosamine; vitamins, such as folic acid, vitamin B12, biotin (vitamin H), niacin (a water soluble vitamin, part of the vitamin B complex) and pantothentic (part of the vitamin B complex); hormones, such as steroid. This list of target molecules is not intended to be exhaustive or to limit the present invention, but is merely illustrative. All of these target molecules are readily known and available to one of ordinary skill in the art. Also, they may be prepared by readily known procedures.

Formation of a complex between the targeting molecule and a sulfonamide moiety of a given prodrug of interest is readily accomplished. Thus, for example, the folic acid and its analogs can be easily conjugated to sulfonamide moieties by activating the carboxyl group of folic acid, thereby making it reactive with the hydroxyl groups of the sulfonamide moieties of interest to form a covalent ester linking bond. See, for example, S. Wang et al., "Synthesis, Purification, and Tumor Cell Uptake of $^{67}$Ga-Deferoxamine-Folate, a Potential Radiopharmaceutical for Tumor Imaging," Bioconjugate Chem. 7:56–62 (1996); P. S. Low et al., Abstract: "Folate-Mediated Targeting of Antineoplastic Drugs, Imaging Agents and Nucleic Acids to Cancer Cells," Eighth International Symposium on Recent Advances in Drug Delivery Systems, Salt Lake City, Utah, pages 48–50 (Feb. 24–27, 1997). Other ligands can be complexed to sulfonamide moieties using art-recognized covalent coupling techniques. Thus, for example, the amino group of glucosamine can be coupled with the hydroxy, amino, or carboxyl group of the sulfonamide moiety through a carbamate bond via carbonyldiimidazole or other coupling reagents. Therefore, ligands having at least one nucleophilic group, e.g., hydroxy, amino, thiol group, can form the respective complex coupled through an amide, carbonate, carbamate, or thiocarbonate bond.

For example, the first compound in Chart K below is doxorubicin to which is attached a sulfonamide moiety and folic acid; the second compound is melphalan to which is attached a sulfonamide moiety and glucosamine; and the third compound is epirubicin to which is attached a sulfonamide moiety and folic acid.

IN ANOTHER ASPECT OF THE PRESENT INVENTION, a mild enzymatic procedure for the sulfonamide deprotection is provided. The GS$^-$ thiolate formed from GSH by GST at neutral pH, allows the proton on the sulfonamide of the primary amines to not be affected. This procedure can, therefore, be applied to the synthesis of a wide range of primary and secondary amines or their derivatives.

The process of the present invention simplifies the product isolation and purification steps. This deprotecting procedure is useful to carry out the deprotection in aqueous solution with or without water miscible organic solvents and the isolation of the desired amine product or its derivative by extraction with organic solvents. It has been found that concentrations of acetonitrile up to 30% have a minor effect on the sulfonamide cleavage. The enzyme and by-products are water soluble and remain in the aqueous phase.

The process of the present invention also provides a tool for stereoisomer isolation and purification. This enzymatic deprotecting method is a stereoselective process. A given sulfonamide-protected stereoisomer can favorably be deprotected by GST/GSH stereoselectively among the racemic mixture or a mixture of diastereomers of protected amines.

There are two features that emerge from the compounds that are cleaved by the process of the present invention: The first concerns that part of the compound that is regarded as the "electrophilic portion", e.g. which, in the case of the compound of formula G-4 in Chart G below, (which is [R-(R*,R*)]-5-cyano-N-[3-[1-[5,6-dihydro-4-hydroxy-2-oxo-6-(2-phenylethyl) -6-propyl-2H-pyran-3-yl]propyl]-phenyl]-2pyridinesulfonamide), is the p-CN-pyridinylsulfonyl group. This part is rather specific since it always contains moieties capable of withdrawing electrons from the carbon atom undergoing nucleophilic attack by the GS$^-$ thiolate. Compounds that have the p-CN— or the p-NO$_2$-pyridinylsulfonyl groups, and those with the p-NO$_2$- or 2,4 dinitro-phenylsulfonyl groups, or the benzothiazole, or the thiophene linked to a sulfonamide bond, are readily cleavable by the enzyme. Chart A below discloses representative examples of such electron-withdrawing groups.

The second feature regards the portion of the compound that, in the enzymatically formed product, contains the amino group. A variety of structures are accomodated in this portion of the compound; they include primary or secondary amines, amides, azides, urea, and hydrazines. Interestingly, they may have a structure as simple as the —NH$_2$ moiety, as in the example of the compound of formula G-1 in Chart G below (which is 6-ethoxy-2-benzothiazolesulfonamide, or CARDRASE) or as complex as the compound of formula G-4 (named above).

In other words, GST cleavage of the sulfonamide requires that specific electrophilic groups are attached to the sulphonyl group, but allows a broad variety of structures to be in the amino portion of the compound. The latter feature is very important because it allows almost any compound (or drug, as described above for the prodrug sulfonamide derivatives) with a free amino group to be attached to selected sulfonyl moieties. For example, compounds containing a —NH— function for use herein include, but are not limited to, those listed in Chart G. The compound of formula G-1 is 6-ethoxy-2-benzothiazolesulfonamide, or CARDRASE, and it contains a simple amine. The compound of formula G-2 is N-[(p-nitrophenyl)sulfonyl]-acetamide and it contains an amide. The compound of formula G-3 is 2,4-dinitro-N-(3-pyridylmethyl)-benzenesulfonamide and it contains a primary amine. The compound of formula G-4 is [R-(R*,R*)]-5-cyano-N-[3-[1-[5,6-dihydro-4-hydroxy-2-oxo-6-(2-phenylethyl)-6-propyl-2H-pyran-3-yl]propyl]phenyl]-2-pyridinesulfonamide, and it contains a primary aromatic amine. It is also disclosed and claimed in International Publication, WO 95/30670, published Nov. 16, 1995. The compound of formula G-5 is 5-methyl-3-(p-nitrophenylsulfonyl)-2-oxazolidinone, and it contains a secondary amine (carbamate).

The starting compounds of the present invention, which are sulfonamide derivatives, are prepared by a variety of synthetic procedures tailored to the structure of a specific compound to be derivatized, particularly to the nature of the reactive functional group to be linked to the sulfonyl moiety. In general, these compounds are synthesized by reacting the precursor compound with the appropriate sulfonyl chloride reagent in the presence of a suitable base in a nonalcoholic organic solvent such as acetone, acetonitrile methylene chloride, ethyl ether, or other solvents. The base is an organic amine such as aniline, triethylamine or pyridine or sodium carbonate or potassium carbonate, or other bases.

An example of the use of the deprotection process of the present invention is presented in Charts H and I below. The compounds, which appear in Charts H and I, are intermediates of formulas II and CCII in the process disclosed and claimed in U.S. Ser. No. 60/016,840, filed May 8, 1996, titled "Process to Prepare Taxol," which is hereby incorporated by reference herein. The variables in these compounds are as defined in that application. The process for preparing compounds of formula CCII is disclosed at page 28, Examples 8A and 8D of that application, which is specifically incorporated by reference herein. The compounds of Chart H are used to prepare the compounds of Chart I. The compounds of Chart I are then modified according to the process of that invention to obtain the final taxol analog compounds of that invention. The deprotection process of the present invention may be readily used to remove the sulfonamide protecting groups of the compounds of Charts H and I under mild conditions.

In place of the sulfonamide protecting groups used on the compounds in Charts H and I, the following sulfonamide protecting groups of the present invention may be used: 2-chloro-4-nitrophenylsulfonyl, 4-nitro-pyridinylsulfonyl, 4-cyano-pyridinylsulfonyl, 2-$CF_3$-4-nitrophenylsulfonyl, and 4-$CF_3$-pyridinylsulfonyl.

DESCRIPTION OF THE PREFERRED EMBODIMENTS

PREPARATION 1

5-Cyano-2-Pyridinesulfonyl chloride (Refer to Chart F)

The Thiol of formula F-3 (10 mL) is oxidized using chlorine gas in 50% aqueous acetic acid. Chlorine gas is bubbled through the suspension while keeping the temperature between 0 and 5° C. The reaction temperature is kept below 10° C. to avoid decomposing the sulfonyl chloride. The sulfonyl chloride is isolated by a temperature controlled (0 to 5° C.) methylene chloride extraction to protect the sulfonyl chloride. The methylene chloride and water used for the work-up are pre-chilled and the wash tank equipped with a dry ice/acetone bath. The reaction is extracted with methylene chloride and the organic phase washed with water. The sulfonyl chloride/methylene chloride solution is dried over anhydrous sodium sulfate and filtered. The solution may be stored for short periods of time at −80° C. without decomposition.

EXAMPLE 1

Cleavage of [R-(R*,R*)]-5-Cyano-N-[3-[1-[5,6-dihydro-4-hydroxy-2-oxo-6-(2-phenylethyl)-6-propyl-2H-pyran-3-yl]propyl]phenyl]-2-pyridine-sulfonamide (Formula J-1: Refer to Chart J)

The protected title compound of formula J-1 is deprotected by GST/GSH under mild conditions. Incubations of 100 μM of this compound and 500 μM GSH with GST (0.5 mg protein /mL) are carried out in 100 mM phosphate buffer, pH 7.4 for 1 hour, at 37° C. in a volume of 0.5 mL. The cleavage of sulfonamide bond is essentially 100% complete after one hour incubation to yield the compound of formula J-2.

EXAMPLE 2

Cleavage of [R-(R*,R*)]-5-Cyano-N-[3-[1-[5,6-dihydro-4-hydroxy-2-oxo-6-(2-phenylethyl)-6-propyl-2H-pyran-3-yl]propyl]phenyl]-2-pyridine -sulfonamide (Formula J-1: Refer to Chart J)

The following observations were made during in-vivo (animal models) and in-vitro (cell cultures) studies of the metabolic disposition of the title compound. It was found that: (1) the title compound underwent sulfonamide cleavage with release of the deprotected compound of formula J-2 upon in-vitro incubation with rat or human hepatocytes; (2) in in-vivo studies in the rat and dog, the compound of formula J-2 was a major circulating metabolite of the title compound in the blood; and (3) CACO-2 cells, a cell line derived from human colon adenocarcinoma, were capable of producing significant sulfonamide cleavage of the title compound. The cleavage of the title compound was markedly faster in these cells than in normal cells.

Some observations that were crucial in the development of a purification strategy of the enzyme that had the sulfonamidase activity: (1) the enzyme activity was inhibited by sulphydryl reactive reagents; (2) passage of a liver cytosol extract through an ultrafilter of cut-off 30,000 Mr concentrated the activity in the retentate, while a negligible activity-was found in the ultrafiltrate; (3) dialysis of a liver cytosol extract by a dialysis membrane of cut-off 12,000–14,000 resulted in an almost complete loss of activity; (4) addition of the ultrafiltrate mentioned in (2) to the dialyzed cytosol restored the activity that was lost in the dialysis process, an observation that implied that the enzyme responsible for the activity was dependent on a cofactor; and (5) among the cofactors tested, AND, NADP$^+$, ATP, NADPH, GSH, GSSG, only GSH was able to restore activity in the dialysate of (3). The latter observation suggested that GSH immobilized to a resin might be a useful step in the purification of the sulfonamidase. Indeed, most of the activity of 10 ml of rat liver cytosol extract was retained by a GSH-Sepharose column (3.9 ml bed volume), packed and equilibrated in 20 mM Hepes buffer, pH 7.5, while the majority of the cytosolic protein was found in the effluent. After the column was washed extensively with up to 1 mM GSH, it was eluted with 5, 20, and 50 mM GSH. The various fractions were dialyzed against 20 mM Hepes buffer, pH 7.5 and tested for enzymatic activity using the title compound and GSH as substrates; the fractions were then subjected to SDS-PAGE. It was found that the fractions containing the activity migrated as a single highly purified band of Mr~25,000. The GSH dependence for activity, the ability to purify the enzyme in a single step by a GSH affinity column, and the Mr~25,000 pointed to Glutathione-S-transferase (GST). Indeed, commercial GST purchased displayed high sulfonamidase activity. The commercial preparation was a mixture of GST isozymes purified from rat liver.

As GST exists in a myriad of isoforms, which are active as homodimers and heterodimers, the specific isozyme(s) which was responsible for sulfonamide bond cleavage in the title compound, was investigated. The commercial isozyme mixture was subjected to RP-HPLC on a $C_{18}$ column (0.45×25 cm). The separation profile of the various isozymes was very similar to that of published work carried out in conditions almost identical to these conditions. Hence the assignment of the various HPLC peaks to isozyme forms was straightforward. The HPLC samples were subjected to lyophilization and refolded in an Na-phosphate buffer at pH 6.8. Alternatively, refolding was carried out by subjecting the HPLC samples to a 16 hours dialysis against Na-phosphate, pH 6.8 followed by a 6 hours dialysis against Na-phosphate, pH 7.4; the refolding process was carried out at 4° C. The title compound's sulfonamidase activity of the reconstituted isozymes was proven for the A3 homodimeric isoform (GSTA3-3), and for the M1 isoform (GSTM1-1) of rat liver cytosol. The identity of the A3 isozyme was confirmed by N-terminus amino acid sequence.

EXAMPLE 3

Cleavage of p-Nitrobenzenesulfonyl azide (Formula J-3: Refer to Chart J)

The protected title compound of J-1 is cleaved upon in-vitro incubation with GST/GSH. Enzymatic cleavage of J-1 yields sulfite ($SO_3^{2-}$), azide ($N_3^-$), and the glutathione-(p-nitrobenzene) conjugate. The metabolism of J-1 was studied in CACO-2 cell culture and shown to yield the same products. Metabolism of J-1 to form the azide was shown to be blocked by known GST inhibitors.

Azide, $N_3^-$, is an agent which is known to be cytotoxic to respiring cells. Azide inhibits ATP production via its interference with the cytochrome electron transport chain involved in the terminal stage of oxidative phosphorylation. The agent is markedly cytotoxic to cells relying on aerobic glycolysis/oxidative phosphorylation as a source of energy. In the presence of GST inhibitors, J-1 was shown to be relatively non-cytotoxic. Metabolism of J-1 within cells by GST releases the potent azide cytotoxin. Thus, covalent coupling of azide with the p-nitrobenzene sulfonyl moiety masks the cytotoxity of azide until cleavage by GST releases the active cytotoxin.

CHART A

Representative goups that are released by GST/GSH when they are part of sulfonamide bonds:

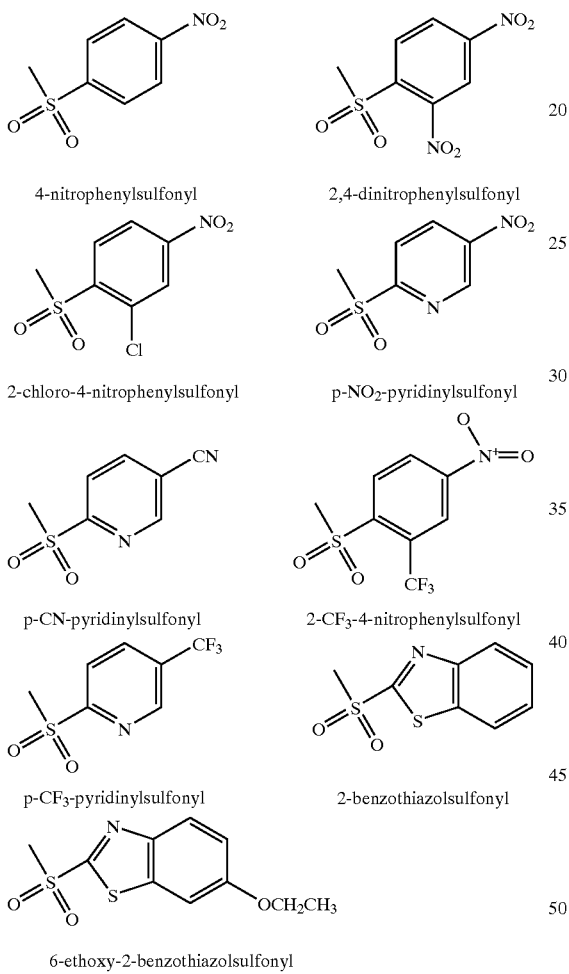

CHART B

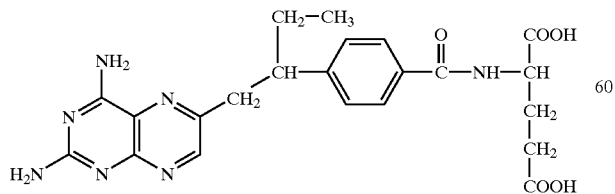

10-ETHYL-10-DEAZA AMINOPTERIN (Edatrexate)

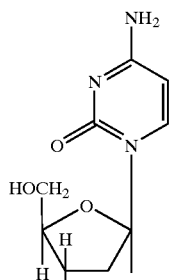

DEOXYCYTIDINE

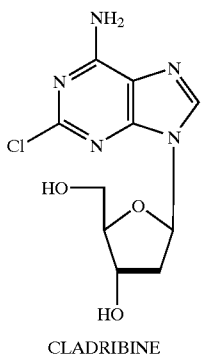

CLADRIBINE

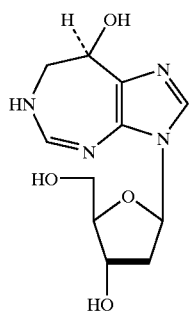

PENTOSTATIN

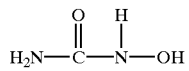

HYDROXYUREA

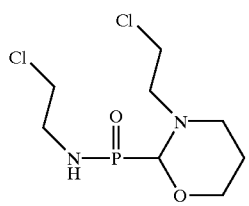

IFOSFAMIDE

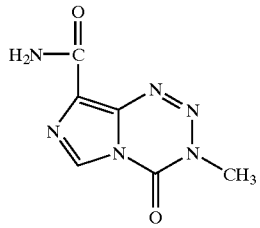

TEMOZOLOMIDI

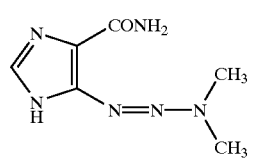

DACARBAZINE

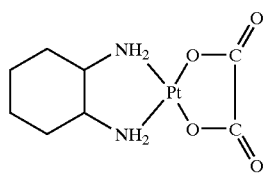

OXALIPLATIN

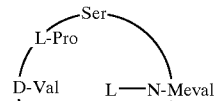

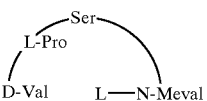

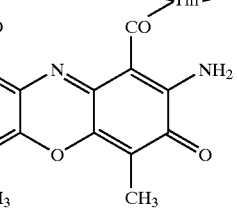

ACTINOMYCIN

-continued
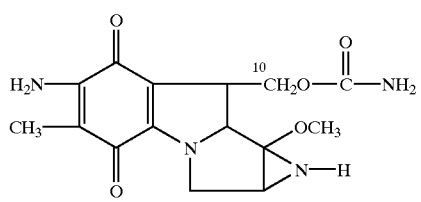
MITOMYCIN C
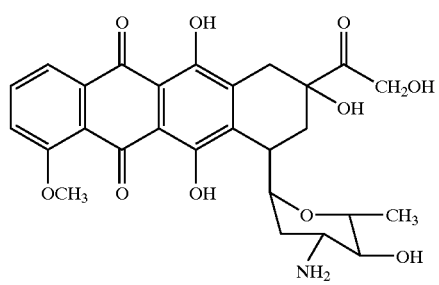
EPIRUBICIN
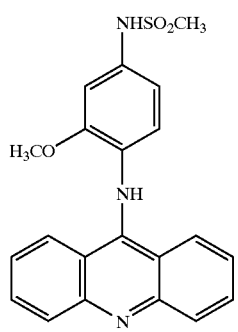
m-AMSA (AMSACRINE)
-continued
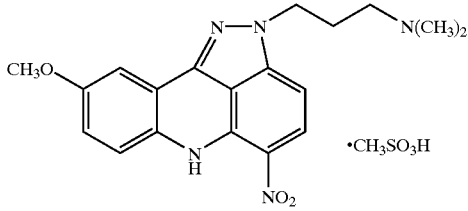
PYRAZOLOACRIDINE
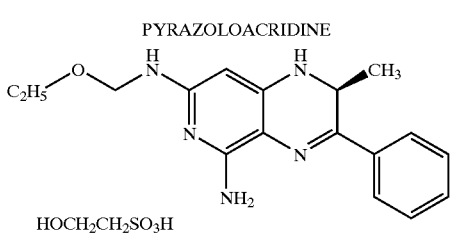
CI-980
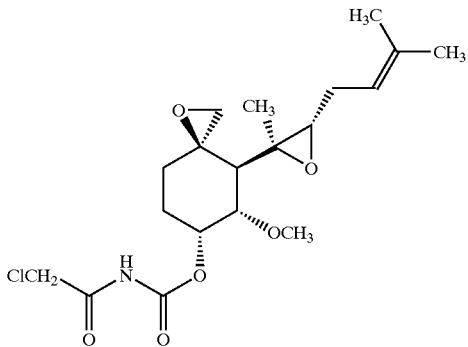
TNP-470
CHART C
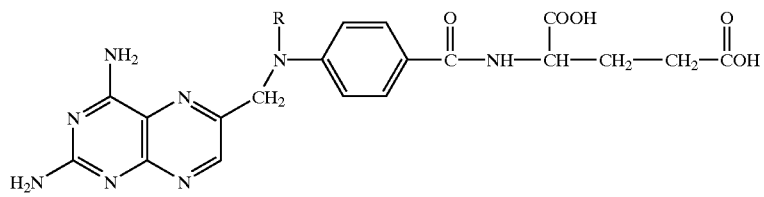
METHOTREXATE R = CH₃
AMIONOPTERIN R = H
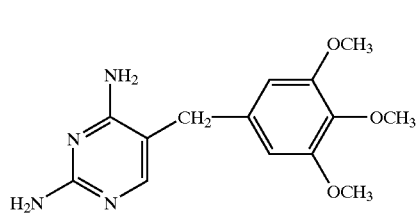
TRIMETHOPRIM
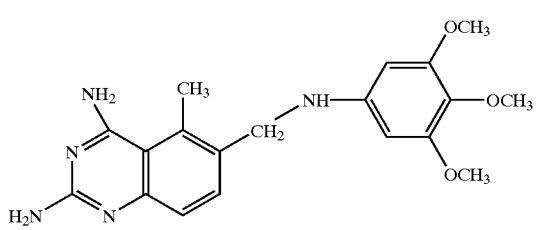
TRIMETREXATE -continued
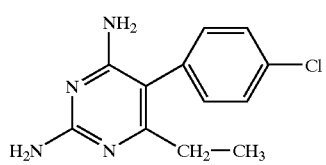
PYRIMETHAMINE
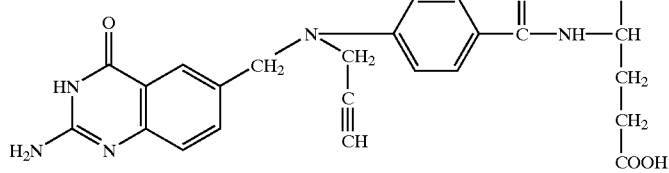
CB 3717
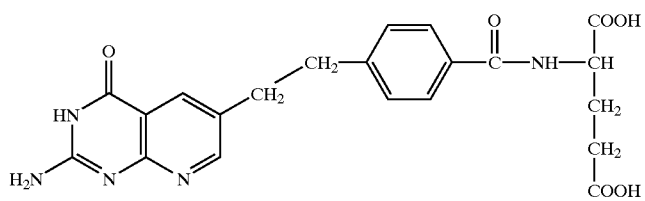
5-10 DIDEAZATETRAHYDROFOLATE
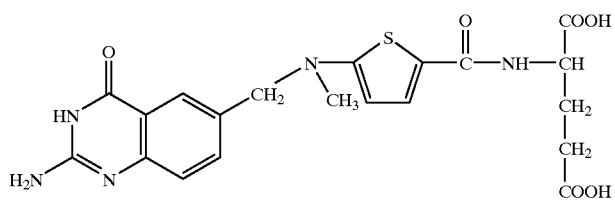
ZD 1694
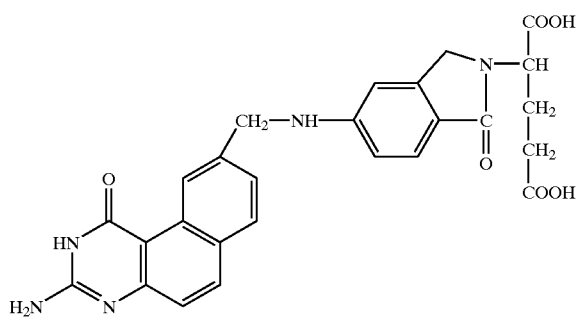
1843U89
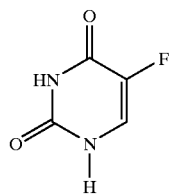
FLUOROURACIL
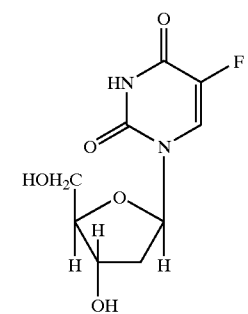
FLUORODEOXYURIDINE
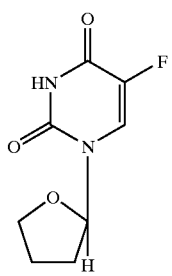
FTORAFUR
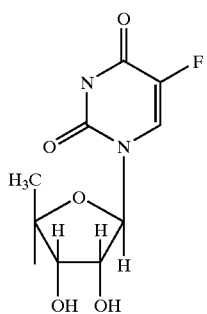
5'-DEOXYFLUOROURIDINE
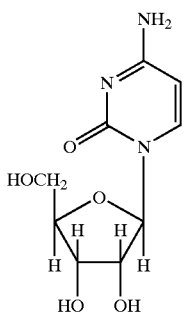
CYTIDINE -continued
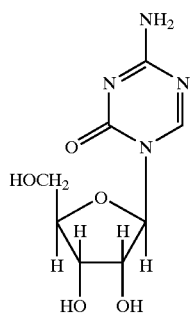
5'-AZACYTOSINE
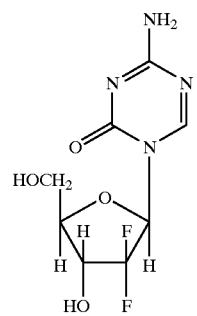
2'-2'-DIFLUORO-DEOXYCYTIDINE
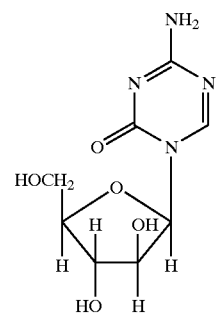
5-AZA-CYTOSINE ARABINOSIDE
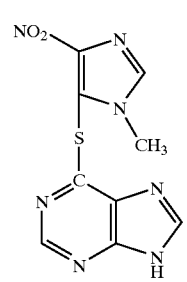
AZATHIOPRINE
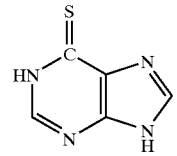
6-MERCAPTOPURINE
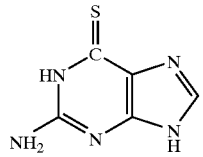
6-THIOGUANINE
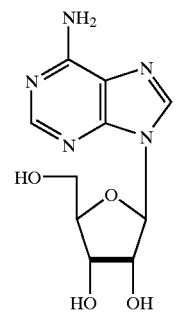
ADENOSINE
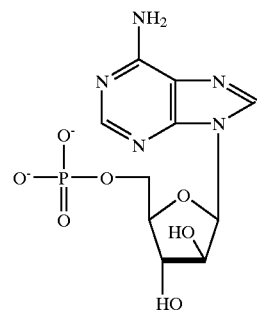
FLUDARABINE PHOSPHATE
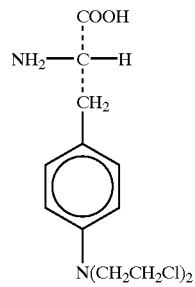
MELPHALAN
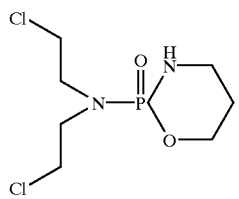
CYCLOPHOSPHAMIDE
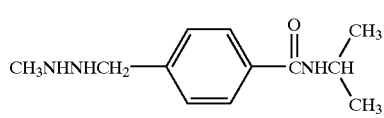
PROCARBAZINE
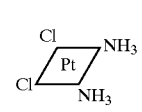
CISPLATIN
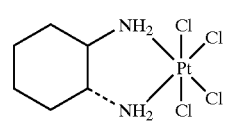
TETRAPLATIN
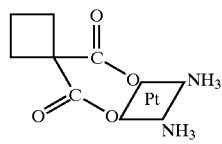
CARBOPLATIN
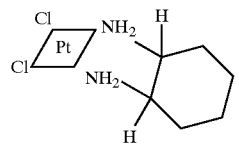
PLATINUM-DACH
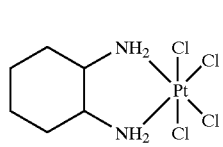
ORMAPLATIN
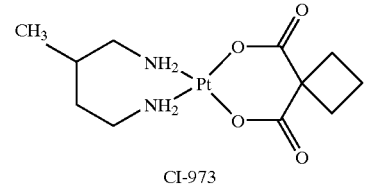
CI-973
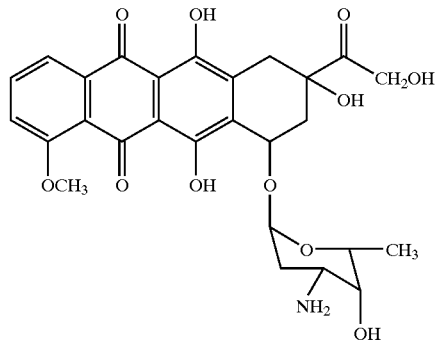
DOXORUBICIN
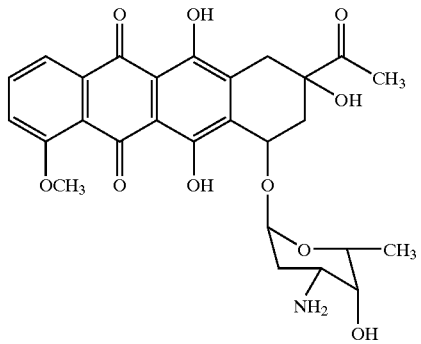
DAUNORUBICIN -continued
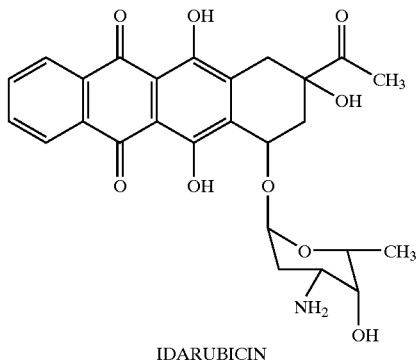
IDARUBICIN
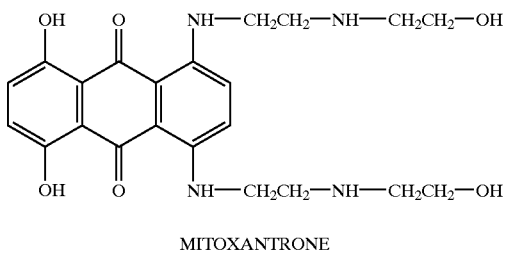
MITOXANTRONE
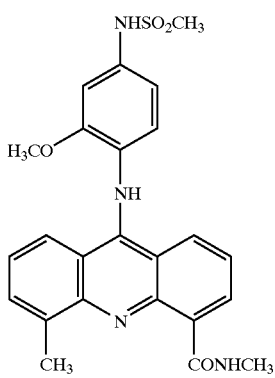
CI-921
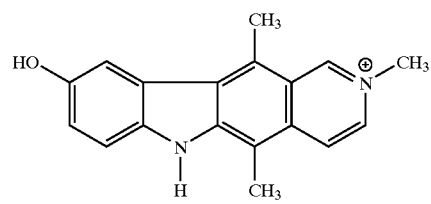
ELLIPTINIUM
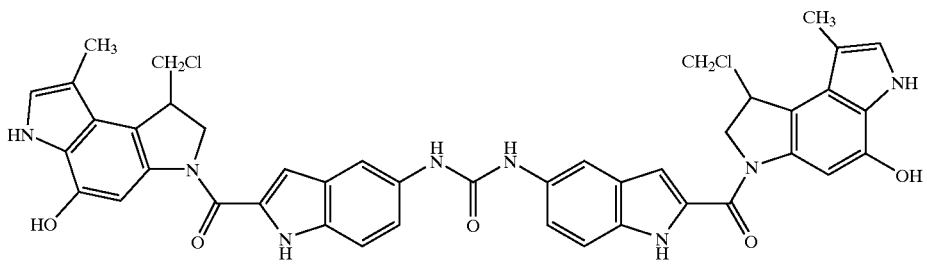
BIZELESIN
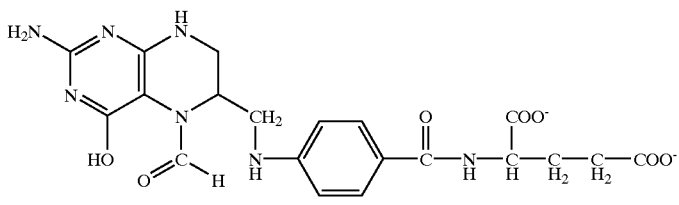
LEUCOVORIN
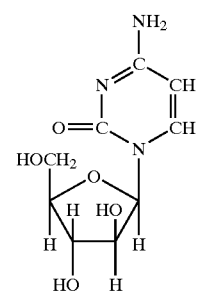
CYTARABINE (ARA-C)

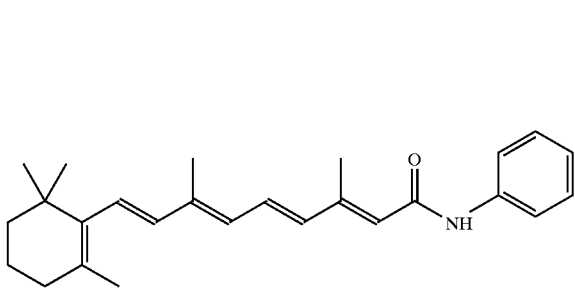
FENRETINIDE
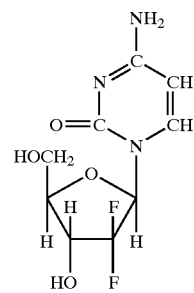
GEMCITABINE (dFdC)
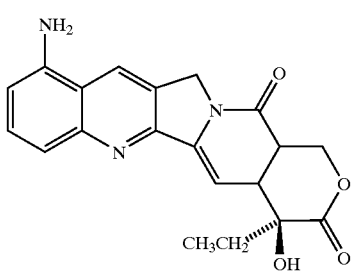
9-AMINOCAMPTOTHECIN
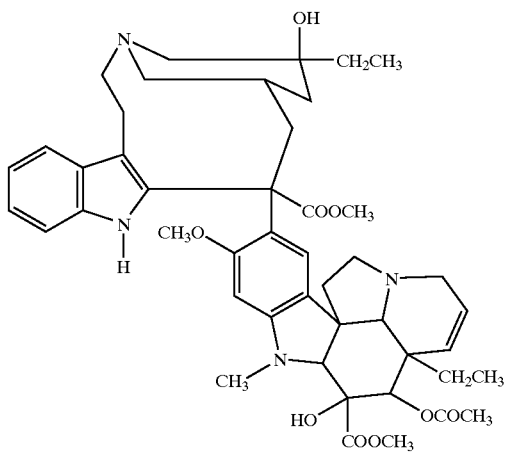
VINBLASTINE
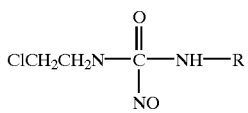
CHLOROETHYLNITROSOUREA
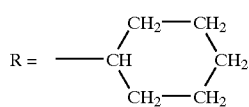
CYCLOHEXYLCHLOROETHYLNITROSOUREA
R = $CH_2CH_2Cl$
BISCHLOROETHYLNITROSOUREA
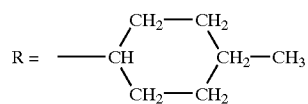
METHYL CYCLOHEXYLCHLOROETHYLNITROSOUREA

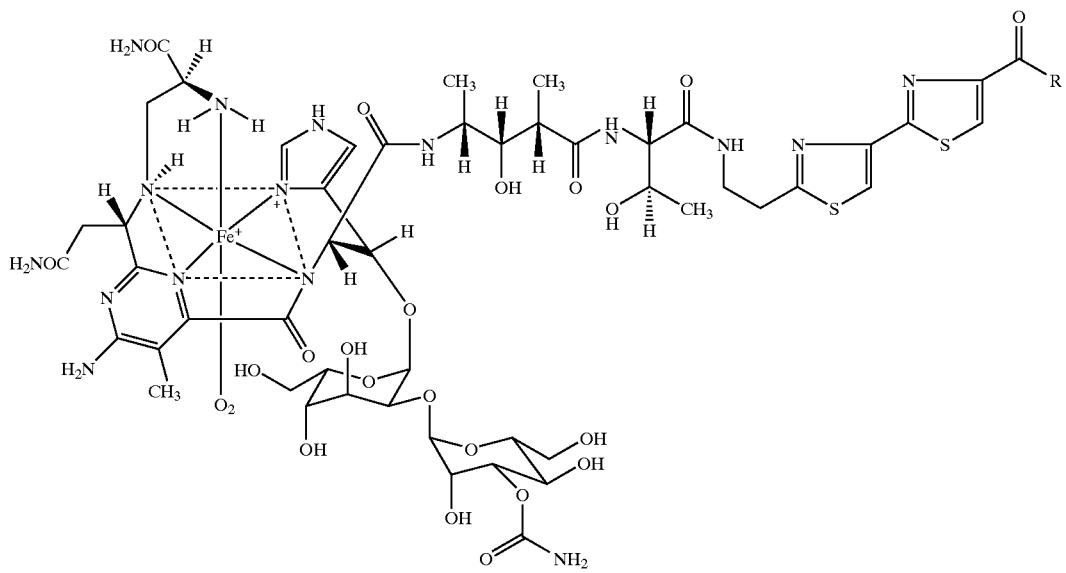
BLEOMYCIN
R:
BLM A2: 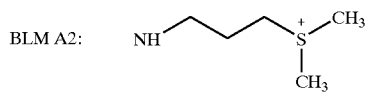
BLM B2: 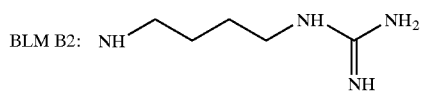
Liblomycin: 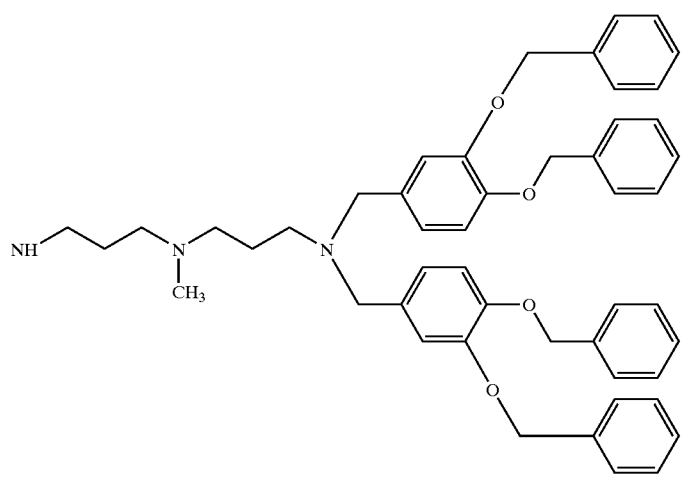

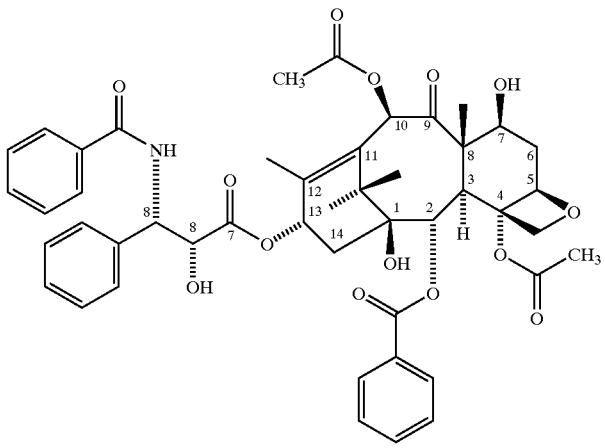

PACLITAXEL

3',4'-DICHLOROBENZOYLALANINE

CHART D

The following generic structure includes compounds derived from an anthracycline in which the carbonyl group of the side chain is also reduced to dihydro or deoxy. In such case, the general formula is:

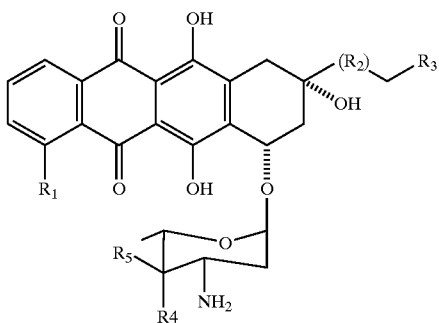

wherein $R_1$ represents hydrogen, hydroxy or methoxy; $R_2$ represents $CH_2$, CO or CHOH, $R_3$ is hydrogen or hydroxy; both $R_4$ and $R_5$ are hydrogen atoms or one of $R_4$ or $R_5$ is hydrogen and the other of $R_4$ or $R_5$ is hydroxy, $C_1$–$C_4$-alkoxy, halogen atom or a group of formula $OSO_2R_6$ in which $R_6$ is $C_1$–$C_6$ alkyl or phenyl.

An embodiment of anthracyclines of the formula above comprises:

daunorubicin (1a: $R_1$=$OCH_3$, $R_2$=CO, $R_3$=$R_5$=H, $R_4$=OH)

doxorubicin (1b: $R_1$=$OCH_3$, $R_2$=CO, $R_3$=$R_4$=OH, $R_5$=H)

4-demethoxydaunorubicin (1c: $R_1$=$R_3$=$R_5$=H, $R_2$=CO, $R_4$=OH)

4'-deoxydoxorubicin (1d: $R_1$=$OCH_3$, $R_2$=CO, $R_3$=OH, $R_4$=$R_5$=H)

4'-iododoxorubicin (1e: $R_1$=$OCH_3$, $R_2$=CO, $R_3$=OH, $R_4$=I, $R_5$=H)

and the corresponding derivatives in which $R_2$ is HOH or $CH_2$.

CHART E

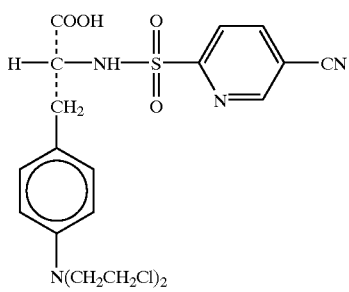

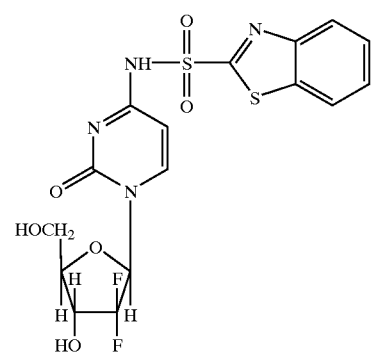

-continued
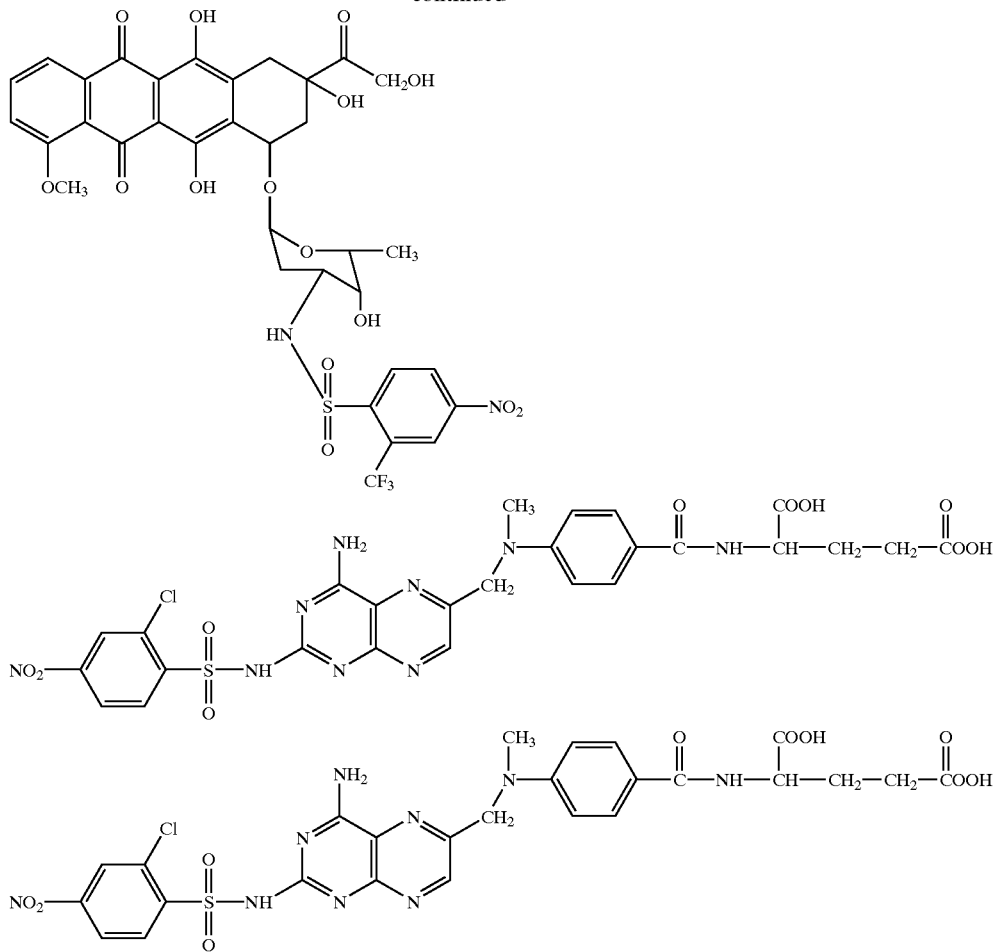
CHART F
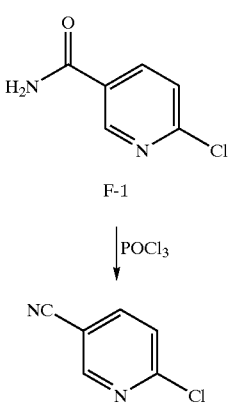
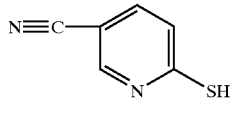
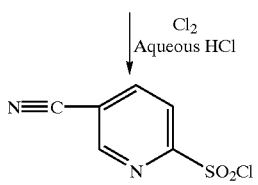
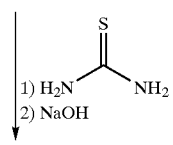
CHART G
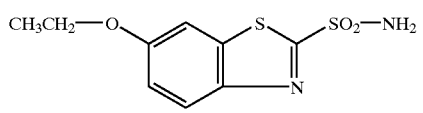

CHART I
(Derived from formula II)
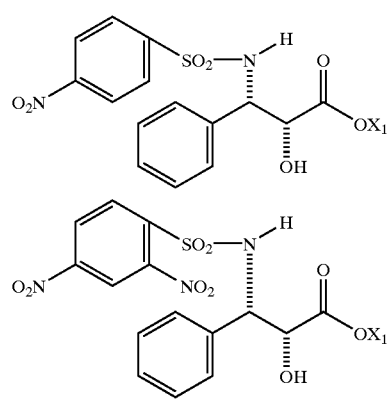
CHART H
(Derived from formula CCII)
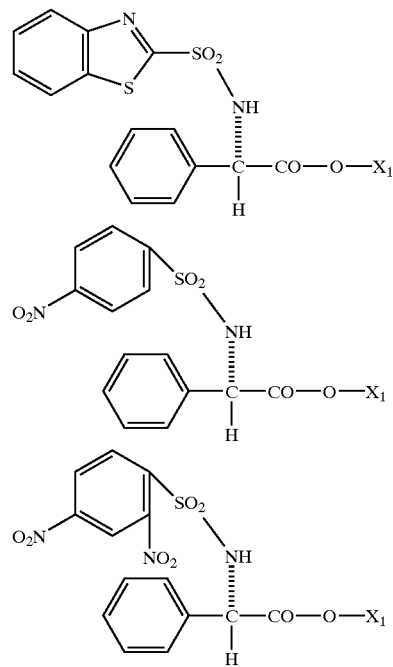
CHART J
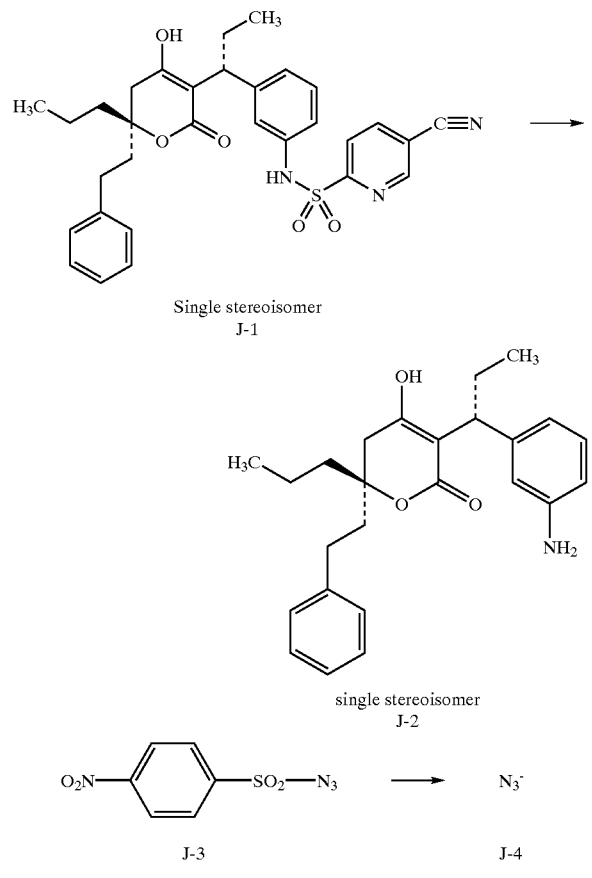

CHART K

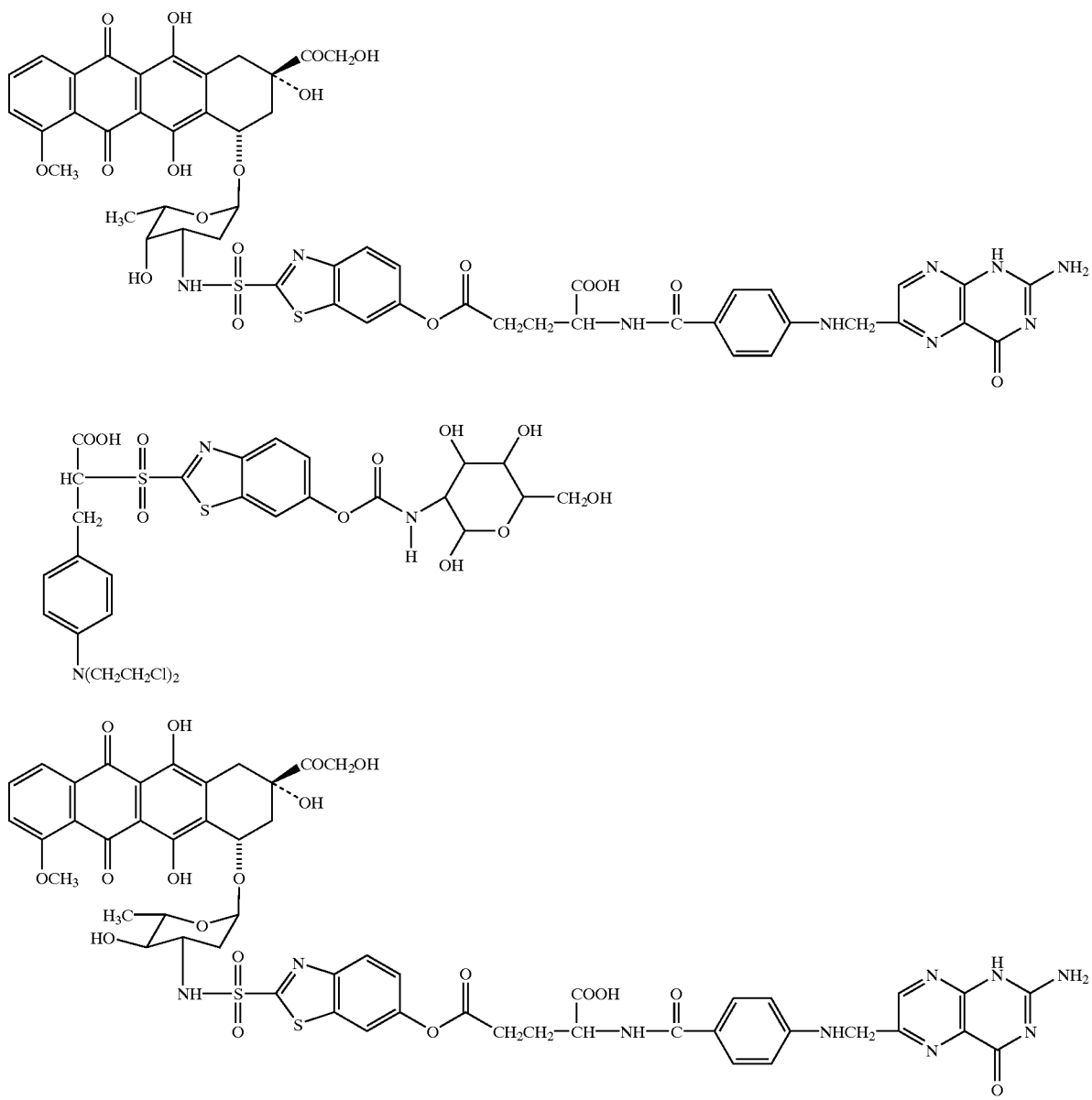

What is claimed is:

1. A method of depleting intracellular Reduced Glutathione (GSH) levels in vivo which comprises utilizing an effective amount of a compound of the formula I

D$_1$-A$_1$      I wherein D1 is Ph—CH(NH)—CH(OH)—COOCH$_3$ or Ph—CH(NH)—COOCH$_3$ and wherein the nitrogen atom of the NH group in D1 being covalently bonded to the sulfur atom of an A$_1$ moiety; wherein the A$_1$ moiety is:

a)
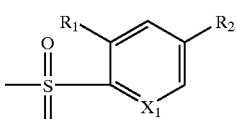

b)
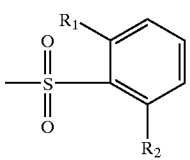

c)

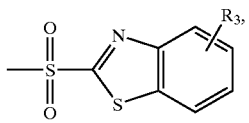

d)

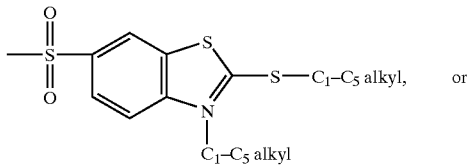

e)

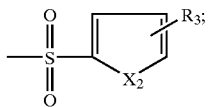

wherein $X_1$ is
a) —C—, or
b) —N—;

wherein $X_2$ is
a) —N—, or
b) —S—;

wherein $R_1$ is
a) —H,
b) —$NO_2$,
c) —Cl,
d) —$CF_3$, or
e) —CN;

wherein $R_2$ is
a) —H,
b) —$NO_2$,
c) —Cl,
d) $CF_3$, or
e) —CN;

wherein $R_3$ is
a) —H,
b) —$C_1$-$C_5$ alkyl,
c) —O—$C_1$-$C_5$ alkyl,
d) —OH,
e) —$NH_2$,
f) —COOH, or
g) —SH;

or a pharmaceutically acceptable salt thereof;

with the following proviso:
1) $R_1$ and $R_2$ are not both —H.

2. A method for depleting intracellular Reduced Glutathione (GSH) levels in vivo which comprises utilizing an effective amount of a compound of the formula I $D_1$-$A_1$      I wherein $D_1$ has an —NH— functional group, the nitrogen atom of the group being covalently bonded to the sulfur atom of an $A_1$ moiety; wherein the $A_1$ moiety is:

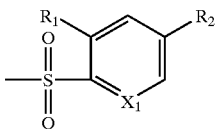

wherein $R_2$ is —CN, $R_1$ is —H, and $X_1$ is —N—;
or a pharmaceutically acceptable salt thereof.

3. A method for depleting intracellular Reduced Glutathione (GSH) levels in vivo which comprises utilizing an effective amount of a compound of the formula I $D_1$-$A_1$      I wherein $D_1$ has an —NH— functional group, the nitrogen atom of the group being covalently bonded to the sulfur atom of an $A_1$ moiety; wherein the $A_1$ moiety is:

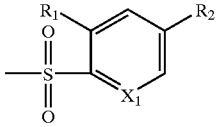

wherein $R_2$ is —$NO_2$, $R_1$ is —H, and $X_1$ is —N—;
or a pharmaceutically acceptable salt thereof.

4. A method for depleting intracellular Reduced Glutathione (GSH) levels in vivo which comprises utilizing an effective amount of a compound of the formula I $D_1$-$A_1$      I wherein $D_1$ has an —NH— functional group, the nitrogen atom of the group being covalently bonded to the sulfur atom of an $A_1$ moiety; wherein the $A_1$ moiety is:

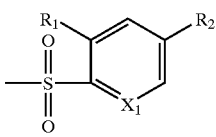

wherein $R_1$ and $R_2$ are both —$NO_2$, and $X_1$ is —C—;
or a pharmaceutically acceptable salt thereof.

5. A method for depleting intracellular Reduced Glutathione (GSH) levels in vivo which comprises utilizing an effective amount of a compound of the formula I $D_1$-$A_1$      I wherein $D_1$ an —NH— functional group, the nitrogen atom of the group being covalently bonded to the sulfur atom of an $A_1$ moiety; wherein the $A_1$ moiety is:

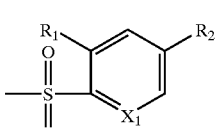

wherein $R_2$ is —$NO_2$, $R_1$ is —H, and $X_1$ is —C—;
or a pharmaceutical acceptable salt thereof.

\* \* \* \* \*